United States Patent
Armstrong et al.

(10) Patent No.: US 10,272,364 B2
(45) Date of Patent: Apr. 30, 2019

(54) SUPERFICIALLY POROUS PARTICLE (SPP) CHIRAL PHASES FOR LIQUID CHROMATOGRAPHY

(71) Applicant: AZYP, LLC, Arlington, TX (US)

(72) Inventors: Daniel W. Armstrong, Arlington, TX (US); Zachary S. Breitbach, Arlington, TX (US)

(73) Assignee: AZYP, LLC, Arlington, TX (US)

( * ) Notice: Subject to any disclaimer, the term of this patent is extended or adjusted under 35 U.S.C. 154(b) by 0 days.

(21) Appl. No.: 15/326,911

(22) PCT Filed: Jul. 17, 2015

(86) PCT No.: PCT/US2015/041026
§ 371 (c)(1),
(2) Date: Jan. 17, 2017

(87) PCT Pub. No.: WO2016/011425
PCT Pub. Date: Jan. 21, 2016

(65) Prior Publication Data
US 2017/0197156 A1   Jul. 13, 2017

Related U.S. Application Data

(60) Provisional application No. 62/025,713, filed on Jul. 17, 2014.

(51) Int. Cl.
*B01D 15/38* (2006.01)
*B01J 20/22* (2006.01)
(Continued)

(52) U.S. Cl.
CPC ........ *B01D 15/3833* (2013.01); *B01J 20/103* (2013.01); *B01J 20/22* (2013.01);
(Continued)

(58) Field of Classification Search
CPC ...... B01D 15/38; B01D 15/3833; B01J 20/24; B01J 20/103
(Continued)

(56) References Cited

U.S. PATENT DOCUMENTS

2012/0226054 A1   9/2012   Miller et al.
2012/0273404 A1   11/2012  Wyndham et al.
(Continued)

FOREIGN PATENT DOCUMENTS

WO    2014087937 A1    6/2014

OTHER PUBLICATIONS

International Search Report dated Oct. 20, 2015 for PCT/US2015/041026.
(Continued)

*Primary Examiner* — Edward M Johnson
(74) *Attorney, Agent, or Firm* — Lucas & Mercanti, LLP

(57) ABSTRACT

The present invention relates to a novel stationary phase support for liquid chromatographic chiral separations. The specific combination of the special underlying support material and certain classes of known chiral selectors according to the invention produces far superior chiral (enantiomeric) separations than those obtained on any conventionally known supports. These chiral (enantiomeric) separations are enhanced in terms of significantly higher efficiencies (theoretical plate numbers), higher resolutions ($R_s$), shorter retention times and either equivalent or slightly higher selectivities than those obtained on conventional supports.

18 Claims, 36 Drawing Sheets

(51) Int. Cl.
- *B01J 20/28* (2006.01)
- *B01J 20/29* (2006.01)
- *B01J 20/32* (2006.01)
- *B01J 20/10* (2006.01)
- *B01J 20/24* (2006.01)
- *B01J 20/283* (2006.01)
- *B01J 20/286* (2006.01)
- *B01J 41/20* (2006.01)
- *C07D 453/04* (2006.01)
- *C07K 9/00* (2006.01)
- *C08B 37/16* (2006.01)
- *C08B 37/00* (2006.01)

(52) U.S. Cl.
CPC ............ *B01J 20/24* (2013.01); *B01J 20/283* (2013.01); *B01J 20/28004* (2013.01); *B01J 20/286* (2013.01); *B01J 20/28016* (2013.01); *B01J 20/28061* (2013.01); *B01J 20/28078* (2013.01); *B01J 20/28083* (2013.01); *B01J 20/29* (2013.01); *B01J 20/3204* (2013.01); *B01J 20/3217* (2013.01); *B01J 20/3246* (2013.01); *B01J 20/3255* (2013.01); *B01J 20/3278* (2013.01); *B01J 20/3293* (2013.01); *B01J 41/20* (2013.01); *C07D 453/04* (2013.01); *C07K 9/008* (2013.01); *C08B 37/0012* (2013.01); *C08B 37/0051* (2013.01); *B01J 2220/52* (2013.01); *C07B 2200/07* (2013.01); *C07B 2200/11* (2013.01)

(58) Field of Classification Search
USPC .......................................................... 502/402
See application file for complete search history.

(56) References Cited

U.S. PATENT DOCUMENTS

2013/0112605 A1   5/2013   Wyndham et al.
2015/0343420 A1   12/2015  Onishi et al.

OTHER PUBLICATIONS

Written Opinion dated Oct. 20, 2015 for PCT/US2015/041026.
T. J. Ward, et al; Chiral separations by high-performance liquid chromatography; Encyclopedia of Analytical Chemistry; Dec. 2012; 25 pages; XP055447105.
K. Gyimesi-Forras, et al; Liquid chromatographic enantiomer separations of novel quinazolone derivatives on . . . ; Journal of Chromatograpy; vol. 1047; No. 1; Aug. 2004; pp. 59-67; XP004527174.
Supplementary European Search Report dated Feb. 2, 2018 for corresponding European Application No. EP 15 82 2332.

| L = linker type (examples) | R = derivative group (examples) |
|---|---|
| Ether | Hydrogen |
| Carbamate | Linear alkane $C_1$-$C_{30}$ |
| Thioether | Branched alkane $C_1$-$C_{30}$ |
| Thiocarbamate | Unsaturated alkane $C_1$-$C_{30}$ |
| Ester | Cyclic alkane $C_1$-$C_{30}$ |
| Triazole | Cyclic or linear alkane with heteroatoms (e.g. N, S, O) $C_1$-$C_{30}$ |
| Urea | Aromatic |
| | Benzyl |
| | Derivatized benzyl (e.g. $NO_2$, Cl, F, Br, $CH_3$ functionalized) |
| | Phenyl |
| | Derivatized phenyl (e.g. $NO_2$, Cl, F, Br, $CH_3$ functionalized) |
| | Naphthyl |
| | Derivatized naphthyl (e.g. $NO_2$, Cl, F, Br, $CH_3$ functionalized) |
| | Biraryl |

FIG. 3 (cont'd)

| L = linker type (examples) | R = derivative group (examples) |
|---|---|
| Ether | Hydrogen |
| Carbamate | Linear alkane $C_1$-$C_{30}$ |
| Thioether | Branched alkane $C_1$-$C_{30}$ |
| Thiocarbamate | Unsaturated alkane $C_1$-$C_{30}$ |
| Ester | Cyclic alkane $C_1$-$C_{30}$ |
| Triazole | Cyclic or linear alkane with heteroatoms (e.g. N, S, O) $C_1$-$C_{30}$ |
| Urea | Aromatic |
| | Benzyl |
| | Derivatized benzyl (e.g. $NO_2$, Cl, F, Br, $CH_3$ functionalized) |
| | Phenyl |
| | Derivatized phenyl (e.g. $NO_2$, Cl, F, Br, $CH_3$ functionalized) |
| | Naphthyl |
| | Derivatized naphthyl (e.g. $NO_2$, Cl, F, Br, $CH_3$ functionalized) |
| | Biraryl |

FIG. 4 (cont'd)

t-butylcarbamoylated cinchona alkaloid

Diameter = 1.7 μm

Diameter = 2.7 μm

Diameter = 4.0 μm

SUPERFICIALLY POROUS PARTICLE (SPP) CHIRAL PHASES FOR LIQUID CHROMATOGRAPHY

CROSS REFERENCE TO RELATED APPLICATION

This Application is a 371 of PCT/US2015/041026 filed on Jul. 17, 2015, which claims priority of U.S. Provisional Application No. 62/025,713 filed Jul. 17, 2014, both of which are incorporated herein by reference.

SUMMARY OF THE INVENTION

The present invention relates to a novel stationary phase support for liquid chromatographic chiral separations. It is the specific combination of the special underlying support material and certain classes of known chiral selectors that produces far superior chiral (enantiomeric) separations than those obtained on any conventionally known supports. These chiral (enantiomeric) separations are enhanced in terms of significantly higher efficiencies (theoretical plate numbers), higher resolutions ($R_s$), shorter retention times and either equivalent or slightly higher selectivities than those obtained on conventional supports.

The classes of known chiral selectors for liquid chromatography include: 1. Macrocyclic types (e.g., cyclodextrins, crown ethers, cyclofructans, antibiotics, peptides, etc.), 2. Pi-complex types (pi-acidic, pi basic and combined), 3. Polymeric types (e.g., proteins, derivatized cellulose or amylose, chiral synthetic polymers, etc.), and 4. Miscellaneous types (ligand exchange, ion exchange, etc.). Examples of the above listed classes are disclosed in the following documents and each of them are incorporated herein by reference: D. W. Armstrong, W. DeMond. *J. Chromatogr. Sci.* 1984, 22, 411, D. W. Armstrong. U.S. Pat. No. 4,539,399, D. W. Armstrong, et al. *Analytical Chem.* 1990, 62, 1610, A. M. Stalcup, et al. *J. Chromatogr.*, 1990, 513, 181, G. D. Y. Sogah and D. J. Cram. *J. Am. Chem. Soc.* 1976, 98, 3038, T. Shinbo, et al. *J. Chromatogr.* 1987, 405, 145, P. Sun, et al. *Anal. Chem.* 2009, 81, 10215, P. Sun and D. W. Armstrong. *J. Chromatogr. A.* 2012, 1217, 4904, D. W. Armstrong, et al. UTA 09-42 US(61341/390761) composition and methods for cyclofructans as separations agents, D. W. Armstrong, et al. *Anal. Chem.* 1994, 66, 1473, D. W. Armstrong. U.S. Pat. No. 5,626,757, A. Berthod, et al. *Anal. Chem.* 2000, 72, 1767, W. H. Pirkle and J. M. Finn. *J. Org. Chem.* 1981, 46, 2935, W. H. Pirkle, et al. *Chirality* 1991, 3, 183, W. H. Pirkle and C. J. Welch, *J. Liq. Chromatogr.* 1992, 115, 1947, J. Hermansson. *J. Chromatogr.* 1983, 269, 71, S. Allenmark, et al. *J. Chromatogr.* 1983, 269, J. Haginaka, et al. *Anal. Chem.* 1995, 67, 2579, Y. Okamoto, et al. *Chem. Lett.* 1984, 739, Y. Okamoto, et al. U.S. Pat. No. 5,202,433, Y. Okamoto, et al. U.S. Pat. No. 5,679,572, Y. Okamoto, et al. *J. Am. Chem. Soc.* 1981, 103, 6971, Q. Zhong, et al. *J. Chromatogr. A.* 2005, 1066, 55, X. Han, et al. *Chromatographia* 2006, 63, 13, V. A. Davankov and S. V. Rogozhia. *J. Chromatogr.* 1971, 60, 280, M. Lammerhofer and W. Lindner. *J. Chromatogr. A.* 1998, 829, 115. See Table 1 below.

As it turns out, only covalently bonded small to moderate size chiral selectors can be used effectively for the present invention. This is due, in part, to the nature of the underlying support material. Larger polymeric chiral selectors (type 3 above) and adsorbed chiral selectors have been shown to be ineffective (i.e., they show few, if any, of the enhanced separation properties).

Examples of macrocyclic, pi-complex and other miscellaneous types of chiral selectors are discussed in, e.g. U.S. Pat. Nos. 4,539,399, 5,626,757 and 7,648,636, the contents of each of which are incorporated herein by reference. Examples of polymeric types of chiral selectors are discussed in, e.g. U.S. Pat. Nos. 7,327,101, 7,223,334 and 5,679,572, the contents of each of which are incorporated herein by reference.

The underlying support material is referred to as "superficially porous particles" (SPPs) or "core-shell" particles. See, for example, J. J. Destefano, et al. *J. Chromatogr. Sci.* 2008, 46, 254, J. J. Destefano, et al. *J. Chromatogr. A.* 2012, 1258, 76, S. Fekete, et al. *LCGC North America* 2014, 32, 420, U.S. Pat. No. 7,846,337, EP 2008971 and F. Gritti and G. Guichon, *J. Chromatogr. A.* 2014, the contents of each of which are incorporated herein by reference. See also FIGS. 1 and 2 for a schematic and transmission electron micrograph, respectively, of SPPs. It has been used to great advantage for routine, achiral reversed phase separations (for example as C18 or C8 bonded phase materials) or for normal phase separations (as bare silica or a bonded nitrile material). It has never been used successfully for enhanced chiral separations. Indeed in the single attempt to use such a SPP support for a chiral stationary phase, there were no enhanced chiral separations, as disclosed in K. Lomsadze, et al. *J. Chromatogr. A.* 2012, 1234, 50, the contents of which is incorporated herein by reference. We have found that this failure resulted from the attempt to utilize and adsorb a larger polymeric derivatized cellulosic chiral selector. The size, the amount and the thickness of such chiral selectors negated the desired performance enhancements on current superficially porous particle (SPP) supports.

DETAILED DESCRIPTION OF THE INVENTION

We found that the solution for enhanced performance on SPP chiral stationary phases (CSPs) was to use specifically bonded, or irreversibly adsorbed, relatively small to moderate sized chiral selectors to form more "brush" type chiral SPPs. Using this approach, we were able to obtain SPP-CSPs that produced far superior enantiomeric separations to anything previously reported. Indeed, to our surprise, the results indicated that these separations often exceeded the performance predicted theoretically, as disclosed in F. Gritti and G. Guichon, J. Chromatogr. A. 2014, 1348, 87-96, the contents of which is incorporated herein by reference.

TABLE 1

Examples of brush-type chiral selectors.

| Brush-type Chiral Selector Class | Example Chiral Selectors |
| --- | --- |
| Oligosaccharides, cyclic oligosaccharides, and their derivatives | Cyclodextrins Derivatized cyclodextrin Cyclofructans Derivatized cyclofructans |
| Peptides, glycopeptides, macrocyclic glycopeptides, and their derivatives | Teicoplanin Vancomycin Teicoplanin aglycone Ristocetin A Dalbavancin Boromycin |
| pi-Complexes | DNB-phenylglycine DNB-diphenylethylenediamine DNB-N-(1,2,3,4-tetrahydrophenanthren-4-yl)benzamide DNB-1,2-diaminocyclohexane |
| Chiral crown ethers | 3,3'-diphenyl-binaphthyl functionalized 18-crown-6 |

TABLE 1-continued

Examples of brush-type chiral selectors.

| Brush-type Chiral Selector Class | Example Chiral Selectors |
| --- | --- |
| Ligand exchangers | Proline, Penicillamine, Hydroxyproline Quinine |
| Ion exchangers | Derivatized quinine Quinidine Derivatized quinidine |

The specific classes of chiral selectors that have been shown to produce these advantageous, superior chiral SPP separations, are the covalently bonded: 1. Macrocyclic CSPs, 2. Pi-complex CSPs and 4. Some of the miscellaneous ligand exchange and ion exchange CSPs. Examples of these chiral selectors are shown in FIGS. 3-8.

As is shown in the following examples, the inventive SPP-CSPs produce up to seven times higher efficiencies per analysis time (at 3 ml/min flow rate), faster analysis, higher resolutions (Rs), plus equivalent to slightly higher selectivities as compared to standard 5 micron and 3 micron diameter fully porous particles (FPPs). The advantage of SSP-CSPs becomes even more obvious from the viewpoint of plate number and resolution per analysis time. As is shown, this is highly advantageous for both analytical and preparative scale (that use 4 or 5 micron diameter SPPs) separations as well as for supercritical/subcritical fluid chiral chromatography.

Furthermore, SPP based chiral stationary phases will be shown to constitute the most powerful approach to obtain/do ultrafast enantiomeric separations (e.g. in the <1 to 40 sec. range). Such fast separations are important for high throughput screening and for increasing the throughput of preparative separations.

Figure 1:
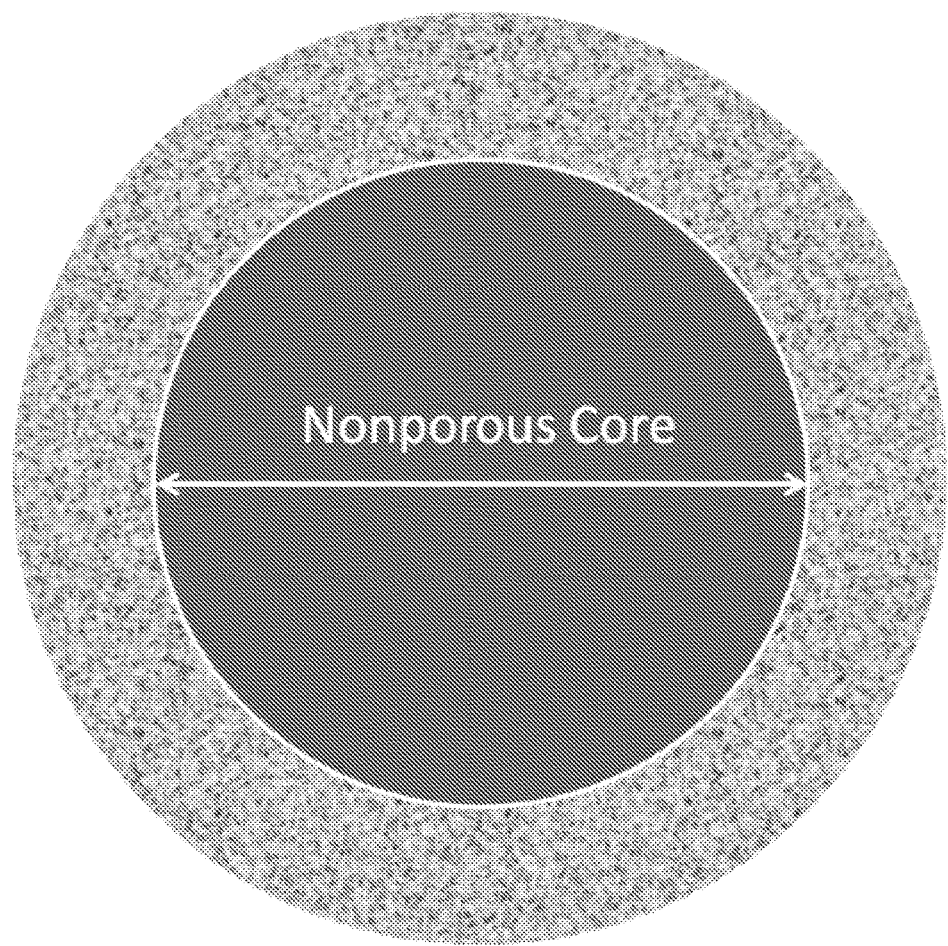
FIG. 1: schematic showing a SPP.
Figure 2:
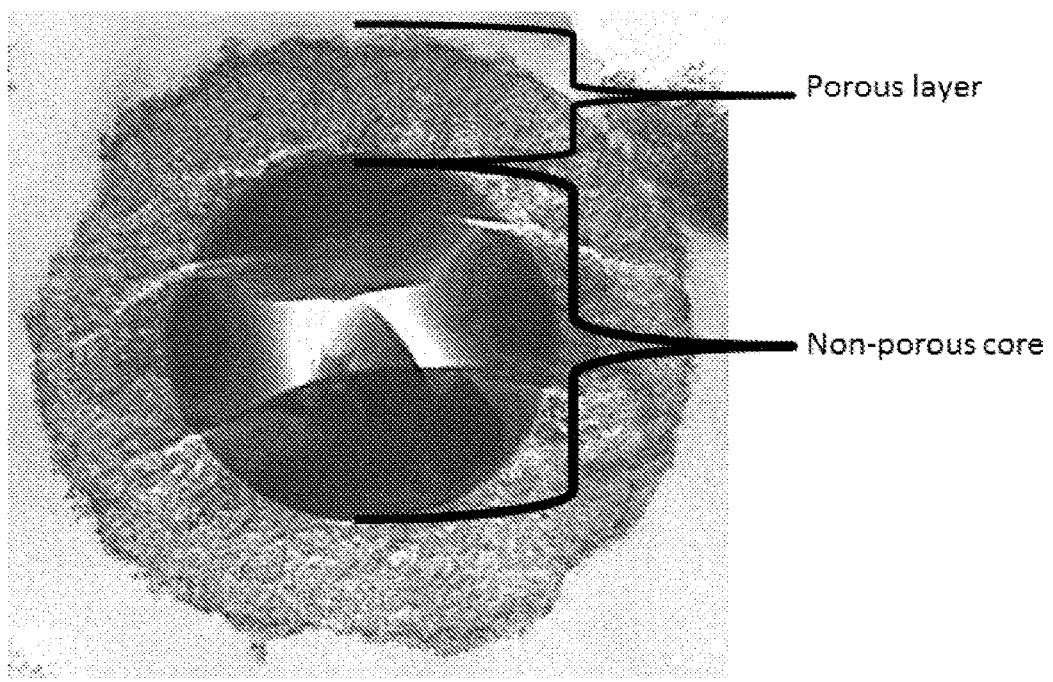
FIG. 2: transmission electron micrograph of a SPP.
Figure 3:
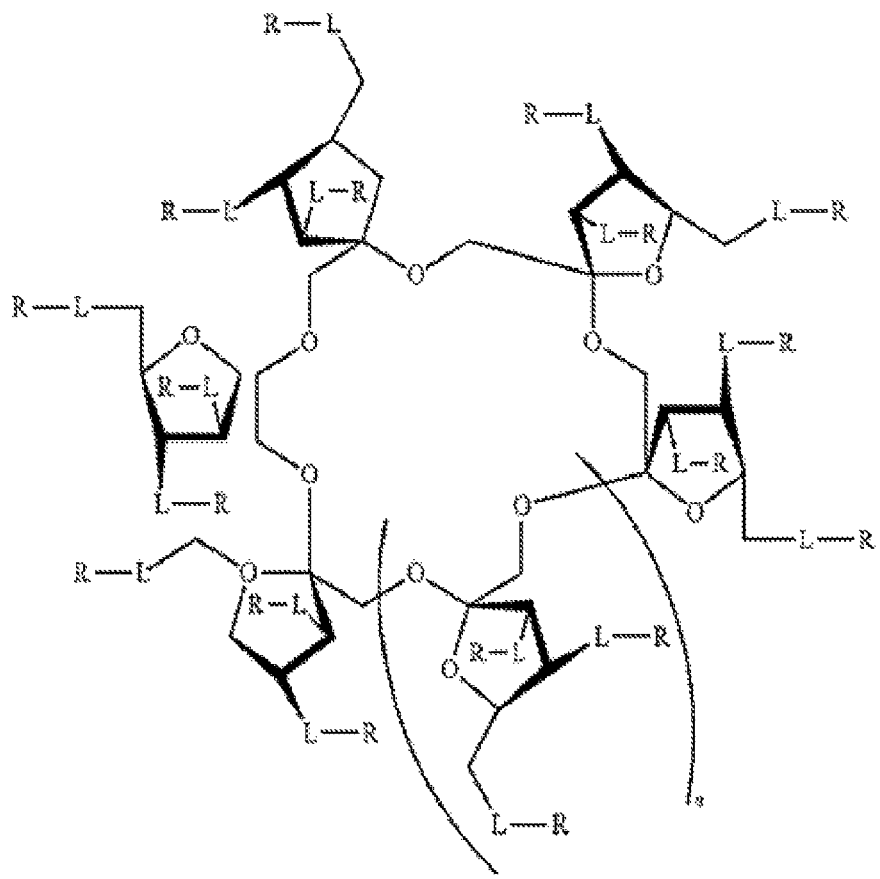
FIG. 3: examples of cyclofructan and cyclofructan derivative chiral selectors.
Figure 4:
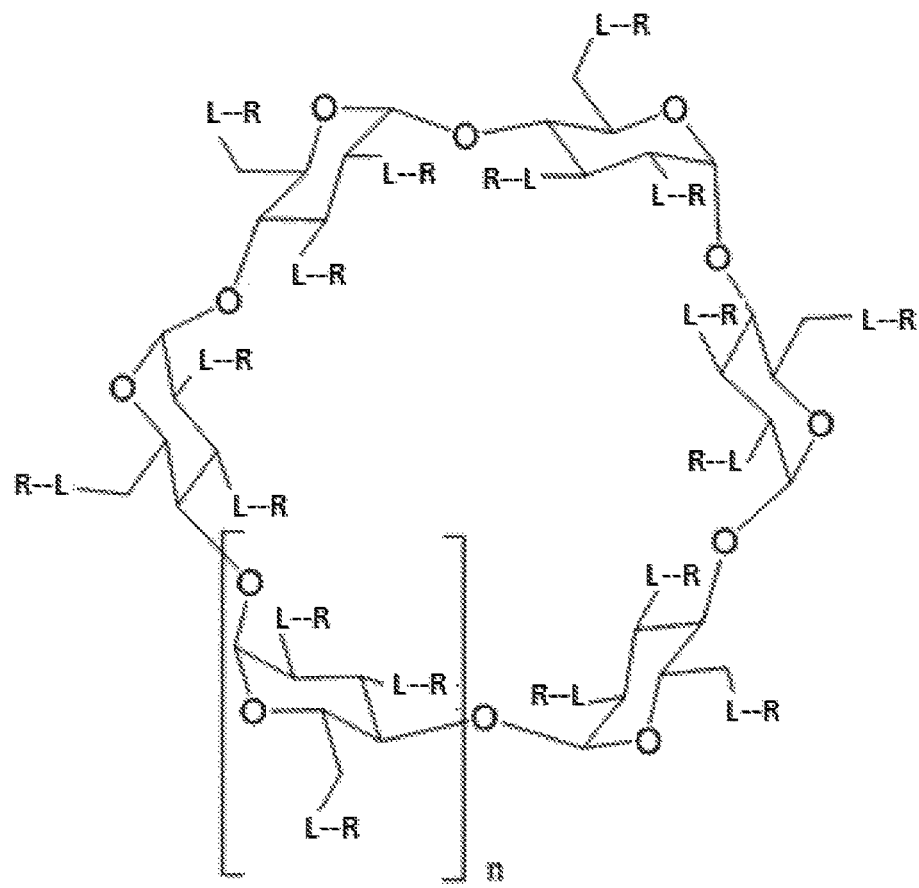
FIG. 4: examples of cyclodextrin and cyclodextrin derivative chiral selectors.
Figure 5:
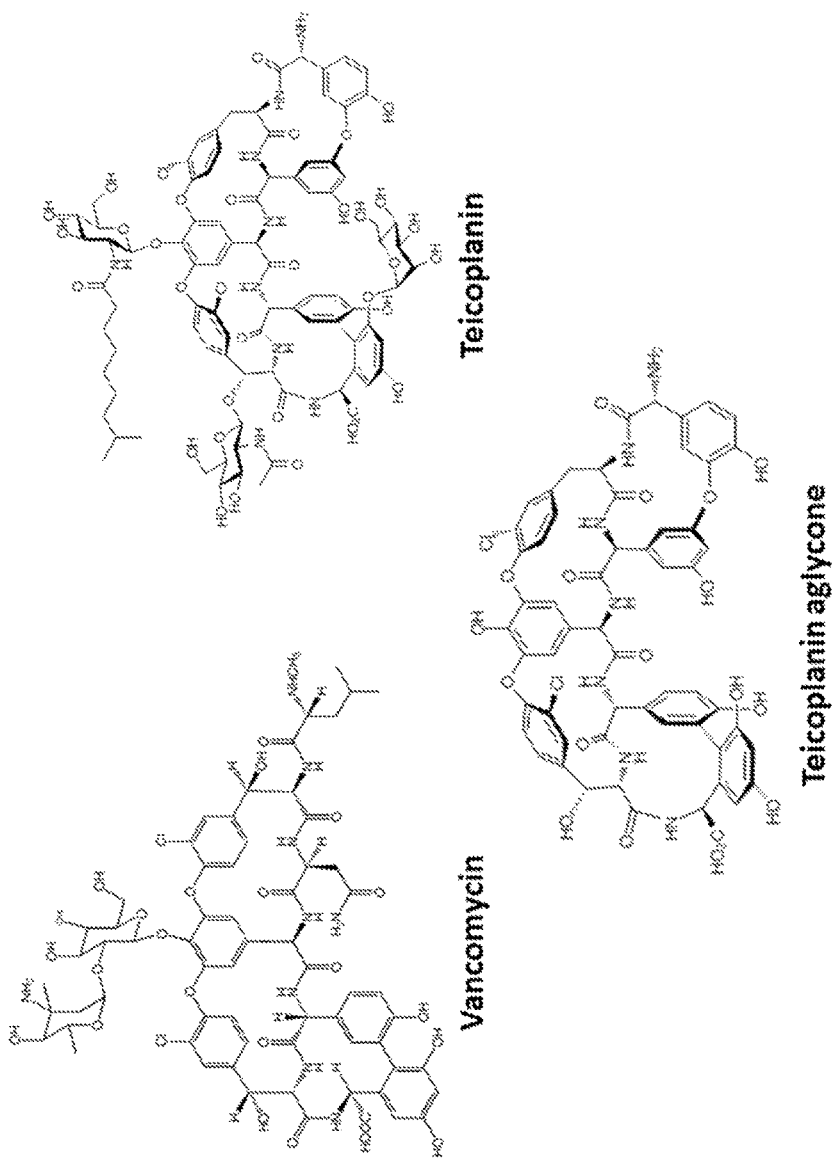
FIG. 5: examples of macrocyclic glycopeptide (antibiotic) chiral selectors.
Figure 6:
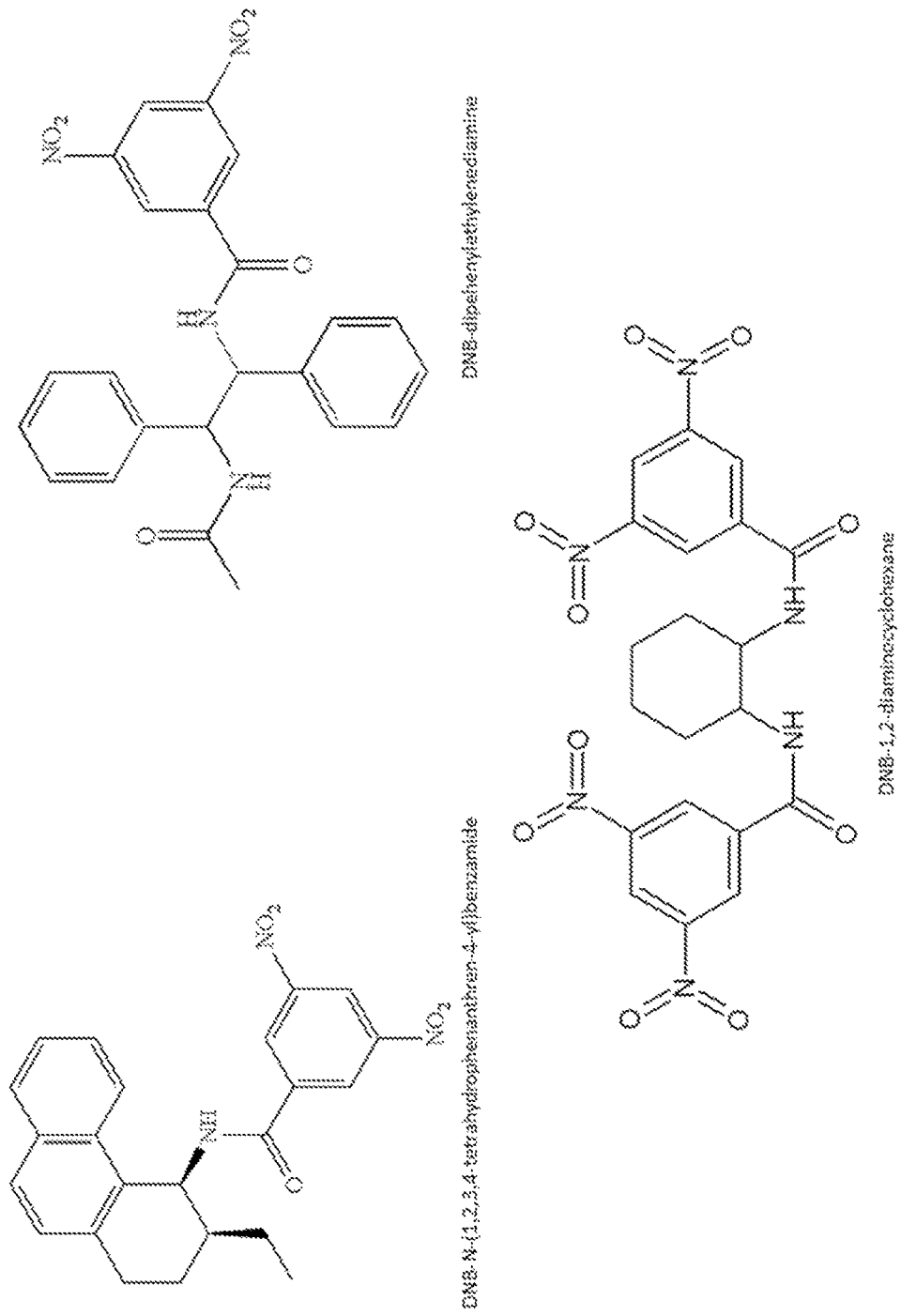
FIG. 6: examples of pi-complex chiral selectors.
Figure 7:
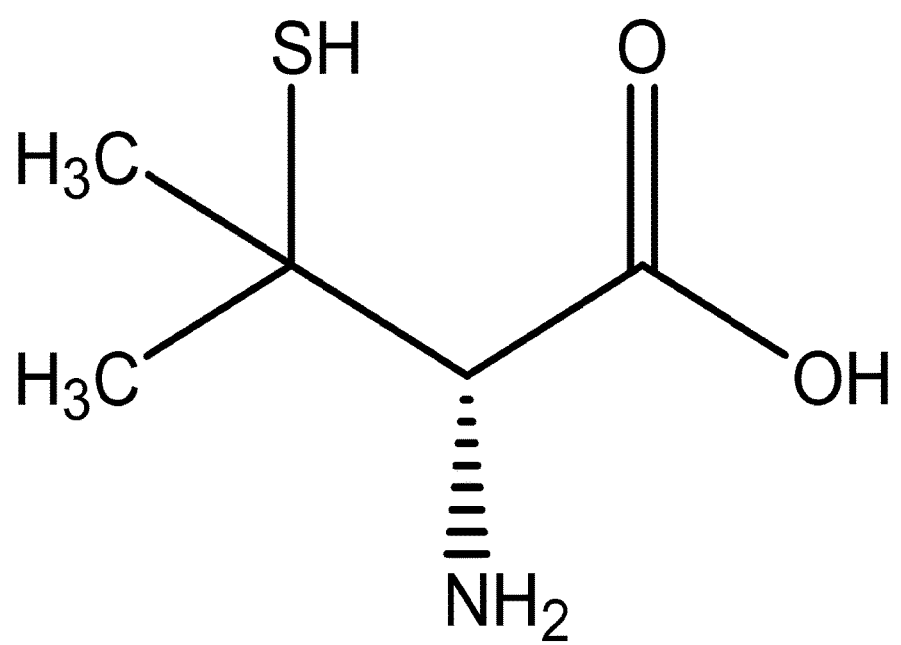
FIG. 7: example of a ligand exchange chiral selector (penicillamine).
Figure 8:
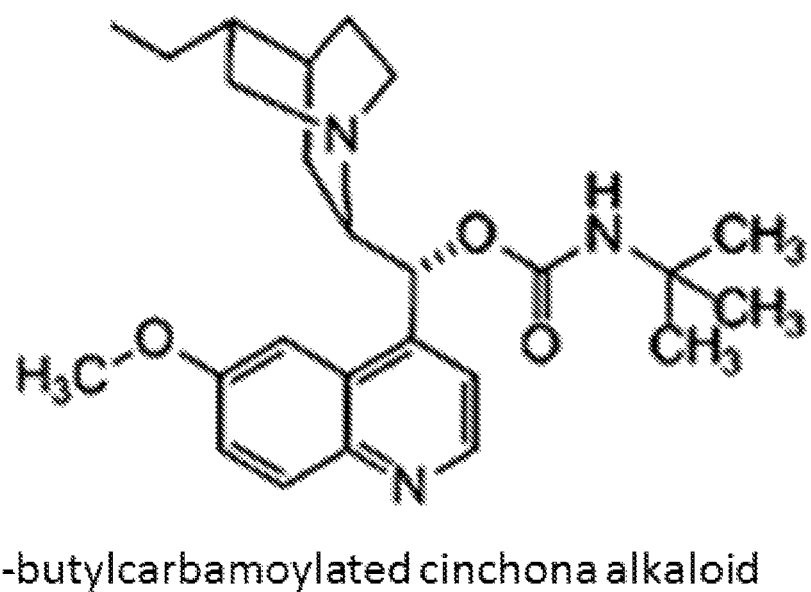
FIG. 8: example of chiral ion-exchange chiral selector.
Figure 9:
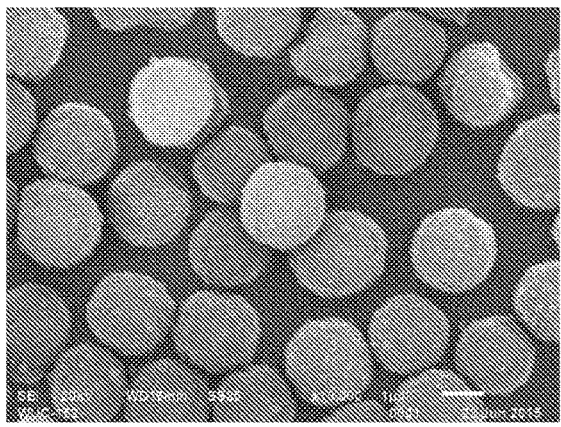
FIG. 9: scanning electron micrographs of examples of 3 different diameter SPPs.
Figure 9:
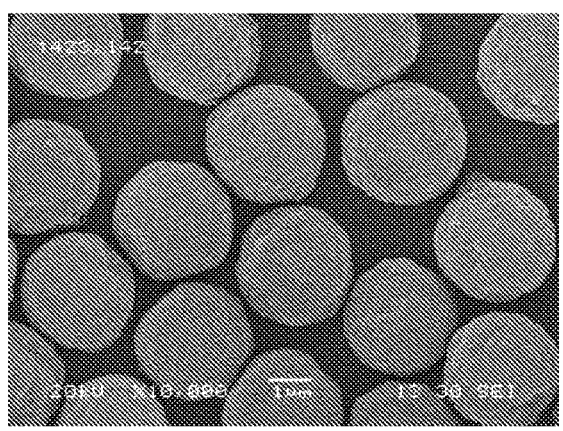
Figure 9:
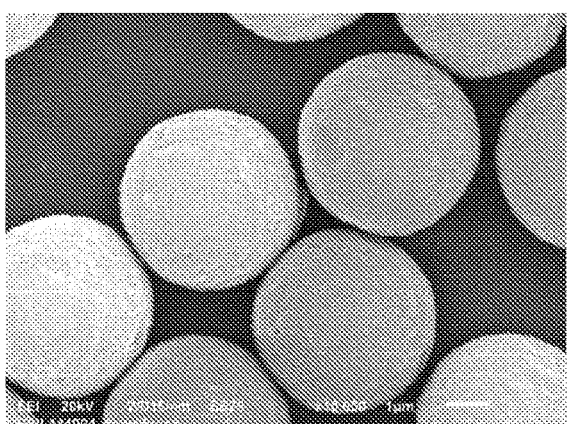

In addition, SPPs have lower surface areas compared to FPPs. As a consequence, one needs less chiral selector (some of which are very expensive) to make a SPP chiral stationary phase that has better performance than traditional FPP-CSPs. Further, such SPP-CSPs can be produced on SPPs that range in size from about 0.5 to about 20 micron in total particle diameter, preferably from about 1.3 to about 10 micron, more preferably from about 1.7 to about 5.0 micron. SPP-CSPs according to the invention can be produced on SPPs having total particle diameter of, for example, about 0.5 micron, about 0.6 micron, about 0.7 micron, about 0.8 micron, about 0.9 micron, about 1.0 micron, about 1.1 micron, about 1.2 micron, about 1.3 micron, about 1.4 micron, and so on. Scanning electron micrographs of some particles, e.g. about 1.7, about 2.7 and about 4.0 micron, are shown in FIG. 9.

In the present application, all CSPs where the performance on SPPs is compared to that on FPPs, were produced using the same chemistry and under the same conditions.

EXAMPLES

Anhydrous toluene, anhydrous pyridine, 3-(triethoxysilyl)propyl isocyanate, (3-glycidoxypropyl) trimethoxysilane, β-cyclodextrin, propylene oxide, dinitrolenzoyl chloride, 3,5-dimethylphenylisocyanate, naphthylethylisocyanate, amlodipine, fipronil, 2'-amino-1,1'-binaphthalen-2-ol (NOBIN), 1,2-diphenylethylamine, acetic acid (AA) and triethylamine (TEA) were purchased from Sigma-Aldrich (Milwaukee, Wis., USA). Cyclofructan 6 was provided by AZYP (Arlington, Tex., USA). Acetonitrile (ACN), heptane, ethanol (EtOH) and methanol (MeOH)

of HPLC grade were obtained from EMD (Gibbstown, N.J.). The fully porous silica with 5 µm of total diameter had an average pore size of 100 Å and average surface area of 465 m$^2$/g. The superficially porous silica particles were 2.7 µm, with 1.7 µm of solid core, 0.5 µm of porous shell, a pore size of 100 Å and 120 m$^2$/g of surface area. The 1.7 µm and 4.0 diameter SPP particles have analogous surface areas and pore sizes.

The isopropyl-substituted cyclofructan chiral stationary phases were synthesized according to procedures described by Sun and Armstrong in P. Sun, et al. *Anal. Chem.* 2009, 81, 10215, P. Sun and D. W. Armstrong. *J. Chromatogr. A.* 2012, 1217, 4904. The cyclodextrin based CSPs were synthesized according to Armstrong as described in U.S. Pat. No. 4,539,399. The macrocyclic antibiotic CSP were synthesized according to Armstrong in U.S. Pat. No. 5,626,757. The π-complex CSPs were synthesized according to Armstrong or Pirkle, see e.g. U.S. Pat. No. 4,539,399, U.S. Pat. No. 5,626,757, W. H. Pirkle and J. M. Finn. *J. Org. Chem.* 1981, 46, 2935 and W. H. Pirkle, et al. *Chirality* 1991, 3, 183. Ligand Exchange CSPs were synthesized by derivatizing penicillamine with dodecylbenzyozl chloride. This purified product was then irreversibly adsorbed onto C18 SPP and C18 FPP for comparison. Ion exchange CSPs were made by immobilizing quinine or quinidine via the method of Lammerhofer and Lindner as provided in M. Lammerhofer and W. Lindner. *J. Chromatogr. A.* 1998, 829, 115. Specific examples of the synthesis of SPP chiral stationary phases are provided below.

Example 1—Preparation of Cyclofructan Based SPP CSPs

Cyclofructans are cyclic oligosaccharides that possess 18-24 hydroxyl groups. These hydroxyl groups can be used as reactive functionalities to covalently bond the cyclofructan (or cyclofructan derivative) to SPP silica. Cyclofructans can be used as chiral selectors in their native form or in a derivatized format. Derivatization of the cyclofructan molecules can take place before or after they are immobilized on the SPP silica. The derivatizing groups are either alkane (e.g. linear alkane C1-C30, branched alkane C1-C30, unsaturated alkane C1-C30, cyclic alkane C1-C30, linear and/or cyclic alkane containing heteroatoms (e.g. N, S, O) C1-C30) or aromatic (benzyl, derivatized benzyl (e.g. NO2, Cl, F, Br, CH3 functionalized), phenyl, derivatized phenyl (e.g. NO2, Cl, F, Br, CH3 functionalized), naphthyl, derivatized naphthyl (e.g. NO2, Cl, F, Br, CH3 functionalized), or biaryl) in nature and are bonded to the cyclofructan by a number of chemical linkages (e.g. ether, carbamate, thioether, thiocarbamate, ester, triazole, and urea).

Native and derivatized cyclofructans are linked to SPP silica in the same way. First, in a 250 mL round-bottom flask cyclofructan (3 mmol) was dissolved in anhydrous DMF (60 mL) under and argon blanket. Then, 3-triethoxysilylpropyl isocyanate (4 mmol) and anhydrous pyridine (5 mL) were added and the reaction vessel was heated to 90° C. for 5 hours. Meanwhile, the SPP silica (4 grams) was first dried in an oven (120° C.) for 4 hours and later azeotropically distilled (toluene, 125 mL) using a Dean-stark trap and a 250 mL, 2-neck round-bottom flask. Once both reaction vessels were allowed to cool to room temperature, the cyclofructan/DMF solution was added to the SPP silica-toluene slurry, and the resulting suspension was refluxed for 16 hours. After that time, the reaction was filtered and washed (toluene, dichloromethane, isopropanol, methanol, water, acetone). This method gives a carbamate linked cyclofructan CSP. The resulting SPP CSP was dried and subsequently slurry packed into a stainless steel tube.

Alternatively, a second binding chemistry which also forms a carbamate linker can be employed. Here, SPP silica (3 grams) was dried at 120° C. for 4 hours. Next, toluene was added and residual water was removed using a Dean-stark trap to azeotropically distill the toluene-SPP silica slurry. The suspension was allowed to cool (<40° C.) and 1 mL of (3-aminopropyl)triethoxysilane was added to the silica (3.3 grams)-toluene (125 mL) slurry and the reaction mixture was refluxed for 4 hours. After which, the suspension was filtered, washed (toluene, dichloromethane, isopropanol, methanol, water, acetone), and dried to yield the amino-functionalized SPP silica. Then, 1,6-diisocyanatohexane (2 mL) was added to a dry amino-silica toluene slurry (under argon), which was cooled with an ice bath. After all the diisocyanate was added, the reaction mixture was heated to 70° C. for 5 hours. After this time, the suspension was filtered, washed (toluene) and finally re-suspended in toluene (anhydrous, 125 mL) and TEA (10 mL). Finally, cyclofructan (1 mmol) was dissolved in anhydrous DMF (25 mL) and the solution was added to the SPP silica suspension and the resulting slurry was refluxed for 16 hours. After that time, the reaction was filtered and washed (toluene, dichloromethane, isopropanol, methanol, water, acetone). This method gives a carbamate and urea linked cyclofructan CSP. The resulting SPP CSP was dried and subsequently slurry packed into a stainless steel tube.

A third bonding strategy will give an example of how cyclofructan and its derivatives can be immobilized with an ether linkage. First, in a 500 mL round-bottom flask cyclofructan (10 mmol) was dissolved in 300 mL of anhydrous DMF under and argon blanket. Then, 1 gram of NaH was added to the solution and the resulting suspension was stirred in an inert environment at room temperature for 30 minutes. Next, any unreacted NaH was filtered off and the filtrate was transferred to a clean, dry, 500 mL round-bottom flask to which 2 mL of 3-glycidoxypropyl trimethoxysilane was added. This solution was heated to 90° C. for 5 hours and then allowed to cool to room temperature. Next, the solution was transferred to a 500 mL 2-neck round bottom flask containing dry SPP silica (21 grams) and the resulting suspension was heated to 110° C. for 16 hours. After that time, the reaction was filtered and washed (toluene, dichloromethane, isopropanol, methanol, water, acetone). The resulting SPP CSP was dried and subsequently slurry packed into a stainless steel tube.

Example 2—Preparation of Cyclodextrin Based SPP CSPs

Cyclodextrins are cyclic oligosaccharides that possess 18-24 hydroxyl groups. These hydroxyl groups can be used as reactive functionalities to covalently bond the cyclodextrin (or cyclodextrin derivative) to SPP silica. Cyclodextrins can be used as chiral selectors in their native form or in a derivatized format. Derivatization of the cyclodextrin molecules can take place before or after they are immobilized on the SPP silica. The derivatizing groups are either alkane (e.g. linear alkane C1-C30, branched alkane C1-C30, unsaturated alkane C1-C30, cyclic alkane C1-C30, linear and/or cyclic alkane containing heteroatoms (e.g. N, S, O) C1-C30) or aromatic (benzyl, derivatized benzyl (e.g. NO2, Cl, F, Br, CH3 functionalized), phenyl, derivatized phenyl (e.g. NO2, Cl, F, Br, CH3 functionalized), naphthyl, derivatized naphthyl (e.g. NO2, Cl, F, Br, CH3 functionalized), or biaryl) in nature and are bonded to the cyclodextrin by a number of chemical linkages (e.g. ether, carbamate, thioether, thiocarbamate, ester, triazole, and urea).

Native and derivatized cyclodextrins are linked to SPP silica in the same way. First, in a 250 mL round-bottom flask cyclodextrin (3 mmol) was dissolved in anhydrous DMF (60 mL) under and argon blanket. Then, 3-triethoxysilylpropyl isocyanate (4 mmol) and anhydrous pyridine (5 mL) were added and the reaction vessel was heated to 90° C. for 5 hours. Meanwhile, the SPP silica (4 grams) was first dried in an oven (120° C.) for 4 hours and later azeotropically distilled (toluene, 125 mL) using a Dean-stark trap and a 250 mL, 2-neck round-bottom flask. Once both reaction vessels were allowed to cool to room temperature, the cyclodextrin/DMF solution was added to the SPP silica-toluene slurry, and the resulting suspension was refluxed for 16 hours. After that time, the reaction was filtered and washed (toluene, dichloromethane, isopropanol, methanol, water, acetone). This method gives a carbamate linked cyclodextrin CSP. The resulting SPP CSP was dried and subsequently slurry packed into a stainless steel tube.

Alternatively, a second binding chemistry which also forms a carbamate linker can be employed. Here, SPP silica (3 grams) was dried at 120° C. for 4 hours. Next, toluene was added and residual water was removed using a Dean-stark trap to azeotropically distill the toluene-SPP silica slurry. The suspension was allowed to cool (<40° C.) and 1 mL of (3-aminopropyl)triethoxysilane was added to the silica (3.3 grams)-toluene (125 mL) slurry and the reaction mixture was refluxed for 4 hours. After which, the suspension was filtered, washed (toluene, dichloromethane, isopropanol, methanol, water, acetone), and dried to yield the amino-functionalized SPP silica. Then, 1,6-diisocyanatohexane (2 mL) was added to a dry amino-silica toluene slurry (under argon), which was cooled with an ice bath. After all the diisocyanate was added, the reaction mixture was heated to 70° C. for 5 hours. After this time, the suspension was filtered, washed (toluene) and finally re-suspended in toluene (anhydrous, 125 mL) and TEA (10 mL). Finally, cyclodextrin (1 mmol) was dissolved in anhydrous DMF (25 mL) and the solution was added to the SPP silica suspension and the resulting slurry was refluxed for 16 hours. After that time, the reaction was filtered and washed (toluene, dichloromethane, isopropanol, methanol, water, acetone). This method gives a carbamate and urea linked cyclodextrin CSP. The resulting SPP CSP was dried and subsequently slurry packed into a stainless steel tube.

A third banding strategy will give an example of how cyclodextrin and its derivatives can be immobilized with an ether linkage. First, in a 500 mL round-bottom flask cyclodextrin (10 mmol) was dissolved in 300 mL of anhydrous DMF under and argon blanket. Then, 1 gram of NaH was added to the solution and the resulting suspension was stirred in an inert environment at room temperature for 30 minutes. Next, any unreacted NaH was filtered off and the filtrate was transferred to a clean, dry, 500 mL round-bottom flask to which 2 mL of 3-glycidoxypropyl trimethoxysilane was added. This solution was heated to 90° C. for 5 hours and then allowed to cool to room temperature. Next, the solution was transferred to a 500 mL 2-neck round bottom flask containing dry SPP silica (21 grams) and the resulting suspension was heated to 110° C. for 16 hours. After that time, the reaction was filtered and washed (toluene, dichloromethane, isopropanol, methanol, water, acetone). The resulting SPP CSP was dried and subsequently slurry packed into a stainless steel tube.

Example 3—Preparation of Glycopeptide Based SPP CSPs

Macrocyclic glycopeptides (e.g. teicoplanin, boromycin, ristocetin A, dalbavancin, and vancomycin) possess amine and hydroxyl functionalities which can be used as reactive groups to covalently bond the glycopeptide (or glycopeptide analog; e.g. teicoplanin aglycone) to SPP silica. There are a number of bonding chemistries that can be used to chemically immobilize macrocyclic glycopeptides on SPP silica (e.g. ether, carbamate, thioether, thiocarbamate, ester, triazole, and urea). The following lists example bonding strategies, using teicoplanin as the model chiral selector.

First, in a 250 mL round-bottom flask teicoplanin (3 mmol) was dissolved in anhydrous DMF (60 mL) under and argon blanket and TEA (3 mL) was added. Then, 3-triethoxysilylpropyl isocyanate (4 mmol) was added and the reaction vessel was heated to 90° C. for 5 hours. Meanwhile, the SPP silica (4 grams) was first dried in an oven (120° C.) for 4 hours and later azeotropically distilled (toluene, 125 mL) using a Dean-stark trap and a 250 mL, 2-neck round-bottom flask. Once both reaction vessels were allowed to cool to room temperature, the teicoplanin/DMF solution was added to the SPP silica-toluene slurry, and the resulting suspension was refluxed for 16 hours. After that time, the reaction was filtered and washed (toluene, dichloromethane, isopropanol, methanol, water, acetone). This method gives a carbamate linked teicoplanin CSP. The resulting SPP CSP was dried and subsequently slurry packed into a stainless steel tube.

Alternatively, a second binding chemistry which also forms a carbamate linker can be employed. Here, SPP silica (3 g) was dried at 120° C. for 4 hours. Next, toluene was added and residual water was removed using a Dean-stark trap to azeotropically distill the toluene-SPP silica slurry. The suspension was allowed to cool (<40° C.) and 1 mL of (3-aminopropyl)triethoxysilane was added to the silica (3.3 grams)-toluene (125 mL) slurry and the reaction mixture was refluxed for 4 hours. After which, the suspension was filtered, washed (toluene, dichloromethane, isopropanol, methanol, water, acetone), and dried to yield the amino-functionalized SPP silica. Then, 1,6-diisocyanatohexane (2 mL) was added to a dry amino-silica toluene slurry (under argon), which was cooled with an ice bath. After all the diisocyanate was added, the reaction mixture was heated to 70° C. for 5 hours. After this time, the suspension was filtered, washed (toluene) and finally re-suspended in toluene (anhydrous, 125 mL) and TEA (10 mL) was added. Finally, teicoplanin (1 mmol) was dissolved in anhydrous DMF (25 mL) and the solution was added to the SPP silica suspension and the resulting slurry was refluxed for 16 hours. After that time, the reaction was filtered and washed (toluene, dichloromethane, isopropanol, methanol, water, acetone). This method gives a carbamate and urea linked teicoplanin CSP. The resulting SPP CSP was dried and subsequently slurry packed into a stainless steel tube.

A third bonding strategy will give an example of how teicoplanin and its derivatives can be immobilized with an ether linkage. First, in a 500 mL round-bottom flask teicoplanin (10 mmol) was dissolved in 300 mL of anhydrous DMF under and argon blanket. Then, 1 gram of NaH was added to the solution and the resulting suspension was stirred in an inert environment at room temperature for 30 minutes. Next, any unreacted NaH was filtered off and the filtrate was transferred to a clean, dry, 500 mL round-bottom flask to which 2 mL of 3-glycidoxypropyl trimethoxysilane was added. This solution was heated to 90° C. for 5 hours and then allowed to cool to room temperature. Next, the solution was transferred to a 500 mL 2-neck round bottom flask containing dry SPP silica (21 grams) and the resulting suspension was heated to 110° C. for 16 hours. After that time, the reaction was filtered and washed (toluene, dichloromethane, isopropanol, methanol, water, acetone). The resulting SPP CSP was dried and subsequently slurry packed into a stainless steel tube.

Example 4—Preparation of Pi-Complex Based SPP CSPs

Pi-complex based SPP chiral stationary phases can be made via a number of binding techniques. Herein, three sample binding strategies are given to produce pi-complex based SPP chiral stationary phases. The first model chiral selector described is dinitrobenzoyl phenylglycine. This example represent a technique that can be used to produce and number of aromatic derivatized amino acid based SPP CSPs.

First, aminopropyl functionalized silica was prepared. SPP silica (20 grams) was placed in a 500 mL 2-neck round-bottom flask and 325 mL of toluene was added. Residual water was removed using a Dean-stark trap to azeotropically distill the toluene-SPP silica slurry. The suspension was allowed to cool (<40° C.) and 1.6 mL of (3-aminopropyl)triethoxysilane was added a silica-toluene slurry and the reaction mixture was refluxed for 15 hours. After which, the suspension was filtered, washed (toluene, dichloromethane, isopropanol, methanol, water, acetone), and dried to yield the amino-functionalized SPP silica. Next, R-(−)-N-(3,5-dinitrobenzoyl)-phenylglycine (5 grams) was dissolved in 100 mL THF and the solution was added to a 2-neck, 250 mL round-bottom flask containing 5 grams of aminopropyl SPP silica. Then EEDQ (4 grams) was added to the suspension and the reaction was stirred at room temperature for 16 hours. After that time, the reaction was filtered and washed (toluene, dichloromethane, isopropanol, methanol, water, acetone). The resulting SPP CSP was dried and subsequently slurry packed into a stainless steel tube.

The DNB-N-(1,2,3,4-tetrahydrophenanthren-4-yl)benzamide chiral selector initially possesses an olefin functionality, which can be used to bond to silica. The following two binding strategies can be applied to any brush-type, pi-complex, chiral selector which has a terminal alkene. The first method requires the direct hydrosilylation of the olefin, which is in turn immobilized on silica. Specifically, the olefin form of DNB-N-(1,2,3,4-tetrahydrophenanthren-4-yl)benzamide was dissolved in DCM (10 mL) and added to a 100 mL round-bottom flask containing IPA (10 mL) and acetic acid (0.5 mL). Then hexachloroplatinic acid (5 milligrams) was added to the flask and the reaction was heated to 65° C. for 30 minutes. The reaction was then cooled to room temperature and triethoxysilane (2 mmol) was added. The resulting solution was heated to reflux for 5 hours, after which the solvent was removed. The ethoxysilylated crude product was dissolved in anhydrous pyridine (25 mL) and added to a SPP silica (4 grams)-toluene (100 mL) slurry. The suspension was refluxed overnight. After that time, the reaction was filtered and washed (toluene, dichloromethane, isopropanol, methanol, water, acetone). The resulting SPP CSP was dried and subsequently slurry packed into a stainless steel tube.

Alternatively, the olefin of the DNB-N-(1,2,3,4-tetrahydrophenanthren-4-yl)benzamide chiral selector can be loaded onto mercapto-functionalized SPP silica through the use of a free radical initiator. To do this, mercaptopropyl silica was first produced by placing SPP silica (20 grams) in a 500 mL 2-neck round-bottom flask with 325 mL of toluene. Residual water was removed using a Dean-stark trap to azeotropically distill the toluene-SPP silica slurry. The suspension was allowed to cool (<40° C.) and 1.6 mL of (3-mercaptopropyl)triethoxysilane was added a silica-toluene slurry and the reaction mixture was refluxed for 15 hours. After which, the suspension was filtered, washed (toluene, dichloromethane, isopropanol, methanol, water, acetone), and dried to yield the mercapto-functionalized SPP silica. Then, the mercaptopropyl SPP silica (6 grams) was slurried in THF (200 mL) and the olefin (4 grams) was added along with AIBN (400 milligrams). The resulting suspension was refluxed for 15 hours. After that time, the reaction was filtered and washed (toluene, dichloromethane, isopropanol, methanol, water, acetone). The resulting SPP CSP was dried and subsequently slurry packed into a stainless steel tube.

Example 5—Preparation of Ion-Exchange Based SPP CSPs

Ion-exchange SPP based CSP can be anionic, cationic, or zwitterionic in nature. Any brush-type chiral selector which is charged and can be bonded to SPP silica can be used as an ion-exchange chiral selector. To be succinct, an example anion exchange chiral selector (t-butyl carbamoylated quinine) will be used as the model CSP. Quinine possesses a hydroxyl group which can be used to bind to SPP silica, but in this case, the hydroxyl group is first derivatized with t-butyl isocyanate. After derivatizing the hydroxyl groups, the quinine still possesses a tertiary amine and a terminal alkene which may be used to bind to SPP silica. To maintain the anion-exchange properties, the amine group should remain free. Therefore, binding of the quinine derivative is done through the terminal alkene. There are two methods used to chemically bond quinine to the SPP silica. The first method requires the direct hydrosilylation of the olefin, which is in turn immobilized on silica. Specifically, the olefin form of t-butyl quinine was dissolved in IPA (10 mL) in a 100 mL round-bottom flask acetic acid (0.5 mL). Then hexachloroplatinic acid (5 milligrams) was added to the flask and the reaction was heated to 65° C. for 30 minutes. The reaction was then cooled to room temperature and triethoxysilane (2 mmol) was added. The resulting solution was heated to reflux for 5 hours, after which the solvent was removed. The ethoxysilylated crude product was dissolved in anhydrous pyridine (25 mL) and added to a SPP silica (4 grams)-toluene (100 mL) slurry. The suspension was refluxed overnight. After that time, the reaction was filtered and washed (toluene, dichloromethane, isopropanol, methanol, water, acetone). The resulting SPP CSP was dried and subsequently slurry packed into a stainless steel tube.

Alternatively, the olefin of the t-butyl carbamoylated quinine chiral selector can be loaded onto mercapto-functionalized SPP silica through the use of a free radical initiator. To do this, mercaptopropyl silica was first produced by placing SPP silica (20 grams) in a 500 mL 2-neck round-bottom flask with 325 mL of toluene. Residual water was removed using a Dean-stark trap to azeotropically distill the toluene-SPP silica slurry. The suspension was allowed to cool (<40° C.) and 1.6 mL of (3-mercaptopropyl)triethoxysilane was added a silica-toluene slurry and the reaction mixture was refluxed for 15 hours. After which, the suspension was filtered, washed (toluene, dichloromethane, isopropanol, methanol, water, acetone), and dried to yield the mercapto-functionalized SPP silica. Then, the mercaptopropyl SPP silica (6 grams) was slurried in THF (200 mL) and the olefin (4 grams) was added along with AIBN (400 milligrams). The resulting suspension was refluxed for 15 hours. After that time, the reaction was filtered and washed (toluene, dichloromethane, isopropanol, methanol, water, acetone). The resulting SPP CSP was dried and subsequently slurry packed into a stainless steel tube.

The chromatographic system used was an Agilent 1260 HPLC (Agilent Technologies, Santa Clara, Calif., USA), consisting of a diode array detector, an auto sampler and a quaternary pump. For all HPLC experiments, the injection volume was 0.5 µL. The mobile phase was degassed by ultrasonication under vacuum for 5 min. The analytes were dissolved in methanol or in the appropriate mobile phases. The stock analyte solution was further diluted with the mobile phase if necessary. The mobile phases used in the polar organic mode, normal phase mode, and the reversed phase mode are listed under each example.

When comparing the performance of different stationary phases, the important parameters are: 1. separation times, 2. efficiency (N or theoretical plate number), 3. selectivity (a), 4. resolution (Rs) and 5. peak shape. The advantages of SPP based chiral stationary phases over conventional fully porous particle (FPP) based chiral stationary phases is that most and often all of these parameters favor SPPs for the types of chiral selectors covered in this patent. The conventional FPP particle used for most chiral separations today is a 5 micron diameter particle. A comparison of such a conventional particle and SPP particle CSP, its properties and chiral selector loading (of isopropyl CF6) are given in Table 2 below.

TABLE 2

Example of particle properties and elemental analysis for CSPs produced on FPPs and SPPs.

| Type | Particle Size (µm) | Pore Size (Å) | Surface Area (m²/g) | C (%) | N (%) | µmol/m²ᵃ | Selector Loadingᵃ (%) |
|---|---|---|---|---|---|---|---|
| FPP | 5 | 93 | 465 | 14.1 | 1.1 | 0.77 | 32.2 |
| SPP | 2.7 | 120 | 120 | 6.2 | 0.9 | 0.88 | 13.1 |

ᵃValues calculated starting with the % C measured by elemental analysis.

According to the invention, SPPs have pore size ranging from about 100 angstroms to about 300 angstroms, preferably from about 100 angstroms to about 150 angstroms, more preferably from about 110 angstrom to about 130 angstrom. SPP according to the invention includes a pore size of about 120 angstrom. Also, according to the invention, SPPs have surface area ranging from about 100 m²/g to about 500 m²/g, preferably from about 100 m²/g to about 400 m²/g, or from about 100 m²/g to about 300 m²/g, or from about 100 m²/g to about 200 m²/g, more preferably from about 110 m²/g to about 150 m²/g. SPP according to the invention has a surface area of about 120 m²/g Note the much lower surface area for the SPP compared to the FPP yet a higher relative coverage (i.e. µmol/m²) of chiral selector actually obtained on the SPPs. This is the more important factor in achieving comparable and often higher selectivities (a) for the nonpolymeric type 1, 2 & 4 CSPs. Also, this shows that far less of expensive chiral selectors are needed to make a column that has superior performance, which is another important parameter for these SPP CSPs.

Figure 10:
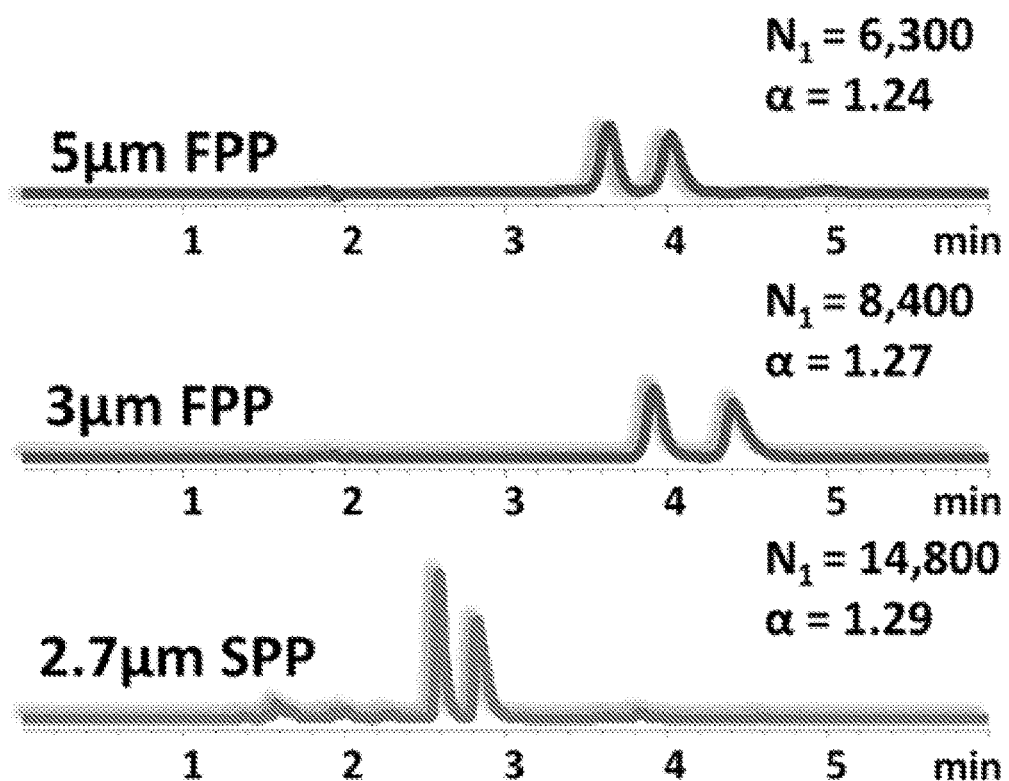
FIG. 10: enantiomeric separation of R/S-phenylpropionic acid.
Figure 11:
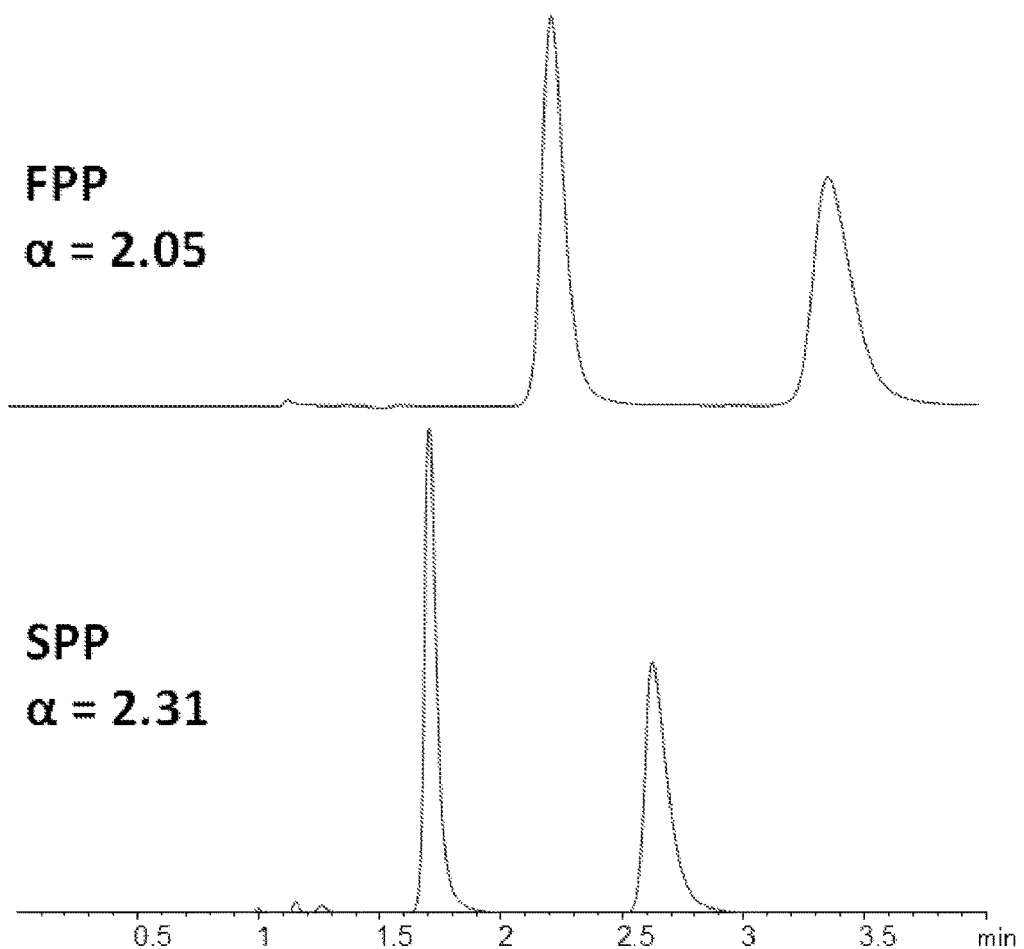
FIG. 11: enantiomeric separation of R/S-mianserine.

Examples showing that the SPP CSPs according to the invention have equivalent to higher enantiomeric selectivity (a) as comparable FPPs are provided in FIGS. 10 and 11. FIG. 10 compares the enantiomeric separation of R/S-phenylpropionic acid using constant mobile phase conditions for the hydroxypropyl-β-cyclodextrin chiral selector bonded to 5 and 3 µm FPPs and 2.7 µm SPPs. It is important to note that the SPP phase not only gave extreme improvements in efficiency, but also gave improved selectivity. The constant mobile phase was 10 mM NH4OAc pH 4.1/ACN 75/25. The flow rate was 1.0 mL/min and detection was UV 254 nm. FIG. 11 provides enantiomeric separation of R/S-mianserine with the vancomycin chiral selector bonded to 5 µm FPPs and 2.7 µm SPPs. It is important to note that the SPP phase gave improved enantiomeric selectivity (a) and shorter retention time. A constant mobile phase of methanol and 0.05% ammonium formate was used. The flow rate was 1.0 mL/min and detection was UV 254 nm.

Data showing the superior reduced plate height (h) for SPP CSP and better peak shapes are provided in the below Tables. Note that the smaller the "h" the better the column can be packed and these produce higher efficiencies, i.e. more theoretical plates.

TABLE 3

Comparison of Theoretical Plates/Meter (N/m), Reduced Plate Height (h), and USP Tailing Factor Using a Standard Achiral Probe 1,3-Dinitrobenzene with 70:30 Heptane-Ethanol at Reduced Velocity of 4.5 (1 mL/min for 2.7 µm SPP, 0.6 mL/min for 5 µm FPP)

| Stationary phase | N/m | h | Tailing factor |
|---|---|---|---|
| Stationary phases bonded to 2.7 µm SPP | | | |
| CF6-P | 172,000 | 2.2 | 1.1 |
| CF7-DMP | 221,000 | 1.6 | 1.2 |
| teicoplanin | 165,000 | 2.3 | 1.0 |
| teicoplanin aglycone | 133,000 | 2.8 | 1.3 |
| vancomycin | 173,000 | 2.1 | 0.9 |
| hydroxypropyl-β-cyclodextrin | 181,000 | 2.0 | 1.3 |
| Commercial columns packed with 5.0 µm FPP (25 × 0.46 cm) | | | |
| LARIHC CF6-P | 70,000 | 2.9 | 1.1 |
| LARIHC CF7-DMP | 59,000 | 3.4 | 1.2 |
| Chirobiotic-T | 54,000 | 3.7 | 0.9 |
| Chirobiotic-TAG | 50,000 | 4.0 | 1.1 |
| Chirobiotic-V | 57,000 | 3.5 | 0.9 |
| Cyclobond I 2000 HP-RSP | 37,000 | 5.4 | 1.1 |

TABLE 4

Data showing the superior reduced plate height (h) and peak shape of SPP. Typically FPP based CSPs have "h-values" in the 3-6 range. A smaller "h" indicates a better packed column.

| Class of CSP and SPP CSP | h | Tailing factor |
|---|---|---|
| Oligosaccharide | | |
| Isopropylated cyclofructan 6 | 2.2 | 1.1 |
| 3,5-Dimethylphenyl cyclofructan 7 | 1.6 | 1.2 |
| Hydroxypropyl-β-cyclodextrin | 2.0 | 1.3 |
| Glycopeptides | | |
| Teicoplanin | 2.3 | 1.0 |
| Vancomycin | 2.1 | 0.9 |
| Teicoplanin aglycone | 2.8 | 1.3 |
| pi-Complex | | |
| DNB-N-(1,2,3,4-tetrahydrophenanthren-4-yl)benzamide | 1.8 | 1.2 |
| DNB-phenylglycine | 1.8 | 1.1 |
| Chiral crown ether | | |
| Cyclofructan 6 | 1.6 | 1.0 |
| Ion-exchange | | |
| Isopropylated quinine | 2.2 | 1.4 |

Figure 12:
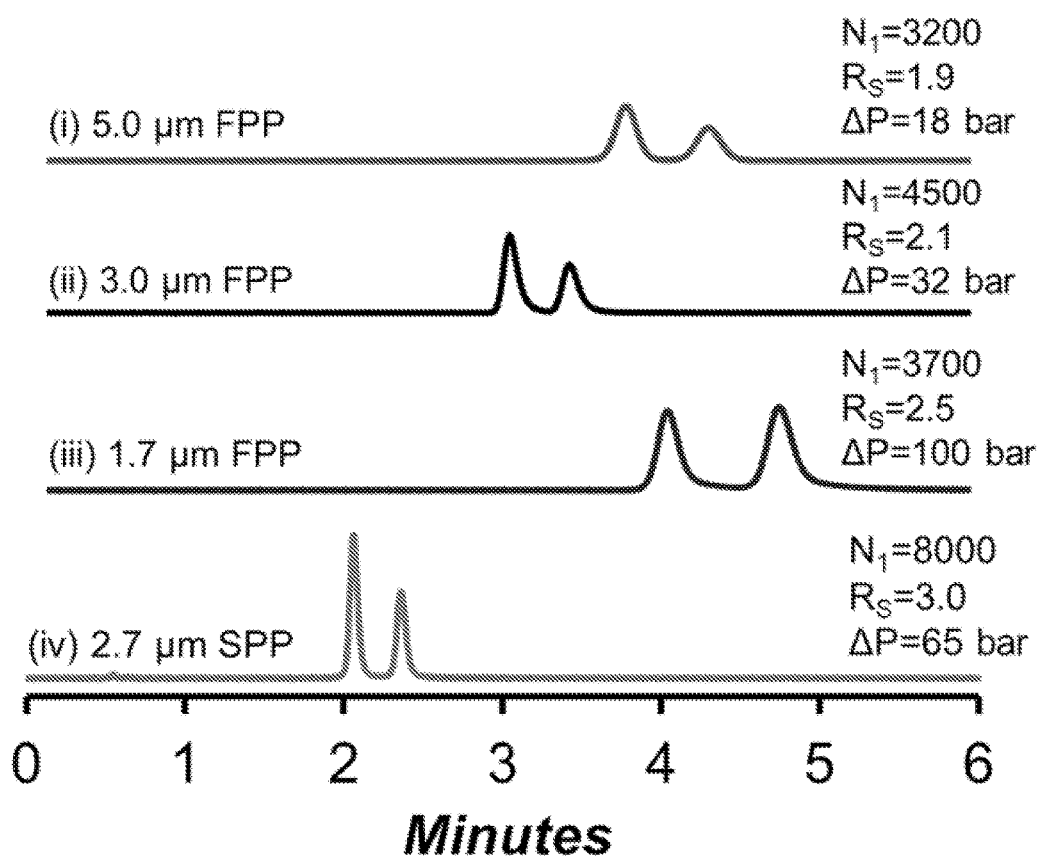
FIG. 12 and FIG. 13: enantiomeric separations of R,S-BINAM.

FIG. 12 shows the superior efficiencies (N), resolutions (Rs) and shorter analyses times for the analysis of enantiomers of R,S-BINAM using a SPP based CSP (bottom curve of FIG. 12) and identical mobile phases. More particularly, FIG. 12 shows enantiomeric separations of R,S-BINAM on isopropylated cyclofructan 6 bonded to SPPs and FPPs at 1.0 mL/min, $T_{col}$=25° C. All columns were 5 cm×0.46 cm in dimensions. A constant MP mode of 92:8 heptane-ethanol as used.

Figure 13:
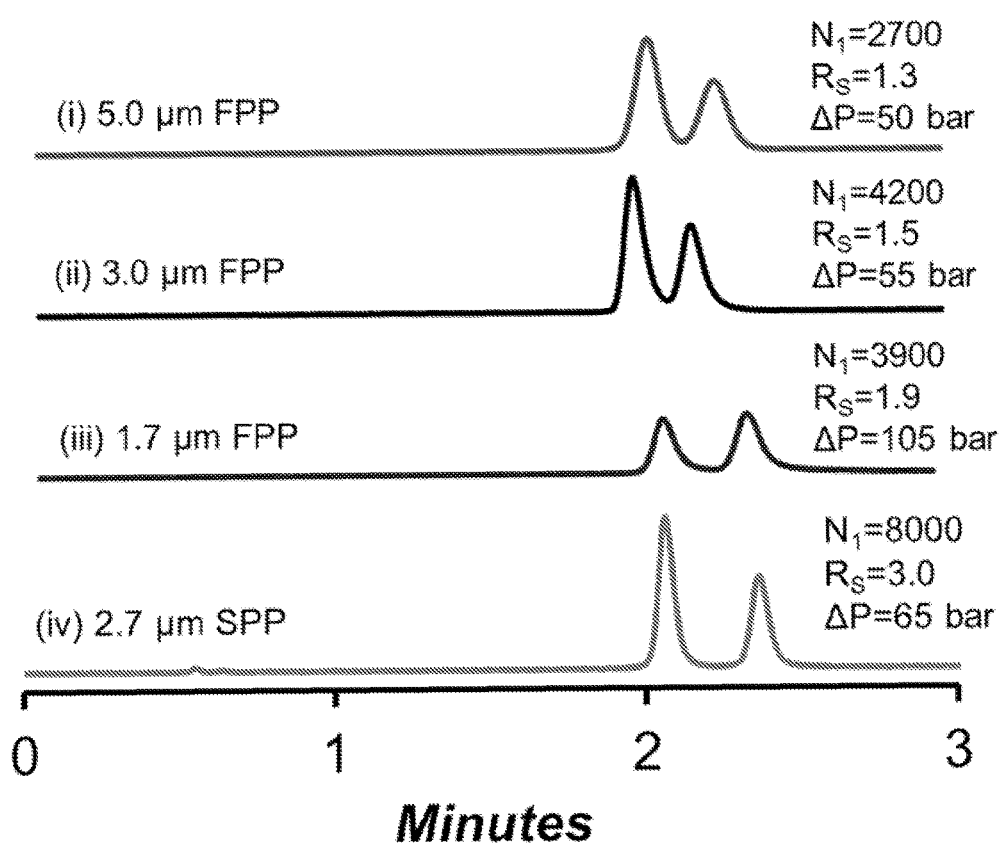

FIG. 13 shows the same separation as FIG. 12 except that the mobile phase compositions have been adjusted to produce equivalent retention times. In this case, the performance of the SPP based CSP (bottom curve) is even higher compared to the fully porous particle (FPP) based stationary phases. These enantiomeric separations were performed with isopropylated cyclofructan 6 bonded to SPPs and FPPs at 1.0 mL/min, $T_{col}$=25° C. All columns were 5 cm×0.46 cm in dimensions. Separations were performed under constant analysis times by alter the mobile phase compositions for each column. MP=(i) 82:18 heptane-ethanol, (ii) 85:15 heptane-ethanol, (iii) 82:18 heptane-ethanol, and (iv) 92:8 heptane-ethanol.

FIGS. 14, 15, 16, 17, 18, 19, 20, 21, 22, 23 and 24 are additional examples of the power of different SPP based CSPs which produce higher efficiencies, higher resolutions and faster analysis time compared to current commercial FPPs that use the same chiral selectors.

Figure 14:
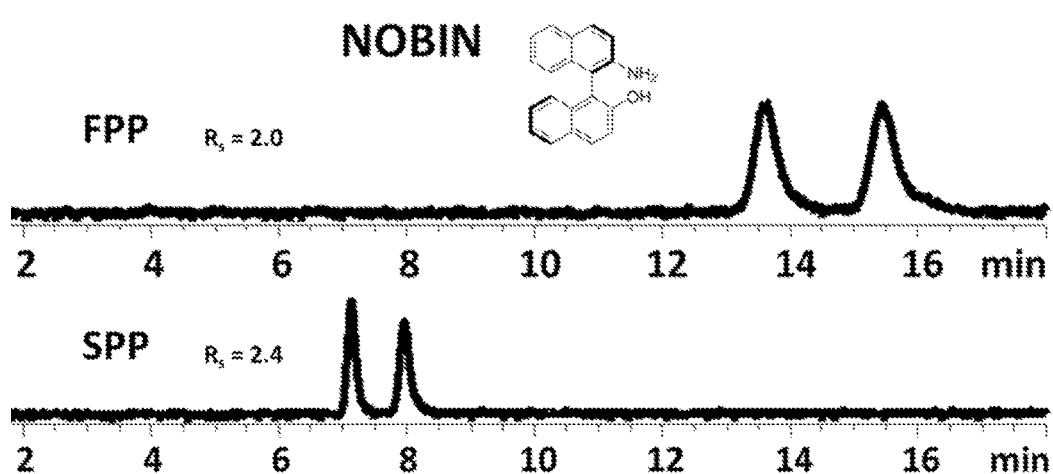
FIG. 14: separation of NOBIN enantionmers.

FIG. 14 shows separation of NOBIN enantiomers using an isopropylated cyclofructan 6 chiral selector bound to FPPs and SPPs. The mobile phase was heptane/ethanol (95/5). Note the resolution observed in both chromatograms, while the separation using the SPP-CSP was complete in nearly half the time. Such an advantage is a result of the increased efficiency afforded by the SPPs, without a concomitant loss of selectivity.

Figure 15:
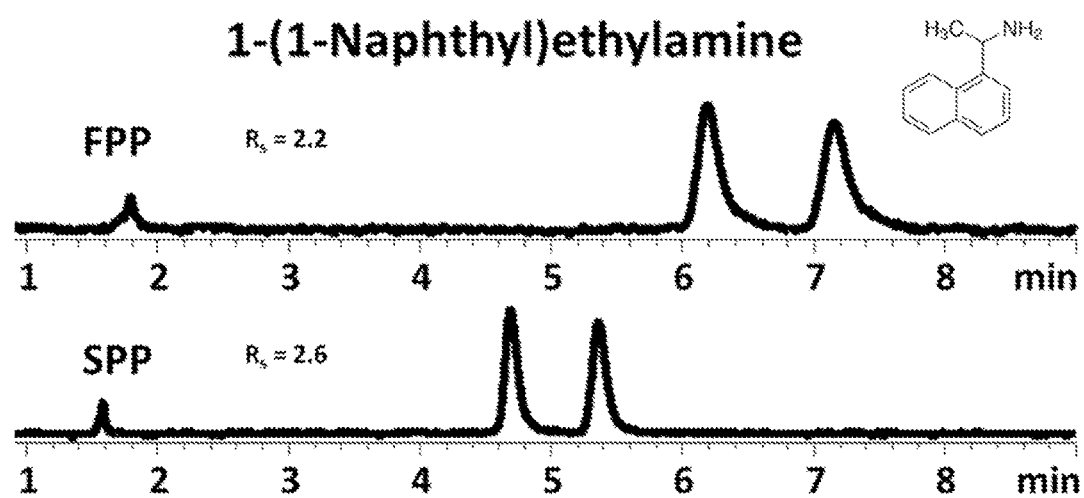
FIG. 15: separation of 1-(1-naphthyl)ethylamine enantiomers.

FIG. 15 shows separation of 1-(1-naphthyl)ethylamine enantiomers using an isopropylated cyclofructan 6 chiral selector bound to FPPs and SPPs. The mobile phase was acetonitrile/methanol (60/40) with 0.3% of acetic acid (AA) and 0.2% triethylamine (TEA). Note the increased resolution and efficiency when using the SPP-CSP. Also, the analysis time was considerably shorter for the separation performed using the SPP-CSP. The advantages include the increased efficiency afforded by the SPPs, without a concomitant loss of selectivity.

Figure 16:
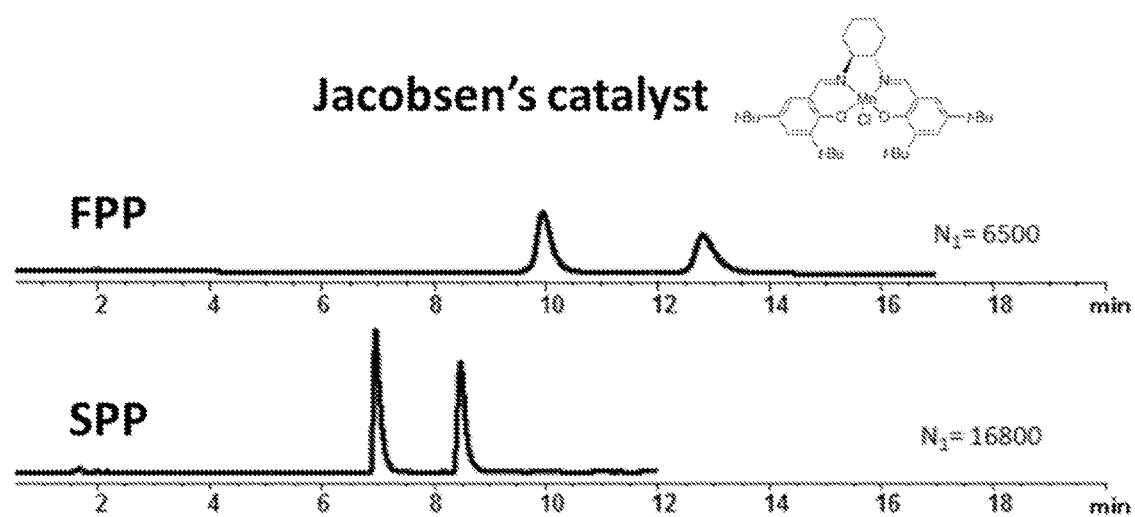
FIG. 16: separation of enantiomers of Jacobsen's catalyst.

FIG. 16 shows separation of the enantiomers of Jacobsen's catalyst using a hydroxypropyl-β-cyclodextrin chiral selector bound to FPPs and SPPs. The mobile phase was ACN/methanol (95/5), flow rate: 1.0 mL/min. Note the better SPP resolution, while the separation using the SPP-CSP was complete in nearly half the time. Such an advantage is a result of the increased efficiency afforded by the SPPs, without a concomitant loss of selectivity.

Figure 17:
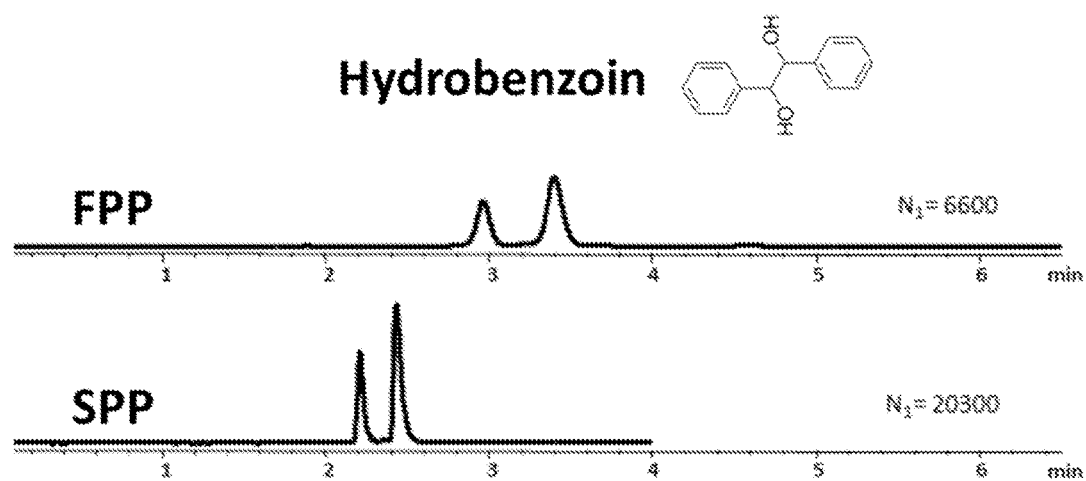
FIG. 17: separation of (RR/SS)-hydrobenzoin enantiomers.

FIG. 17 shows separation of (RR/SS)-hydrobenzoin enantiomers using a hydroxypropyl-β-cyclodextrin chiral selector bound to FPPs and SPPs. The mobile phase was 10 mM NH4OAc (pH 4.1)/ACN (75/25), flow rate: 1.0 mL/min. Note the baseline resolution observed in both chromatograms, while the separation using the SPP-CSP was complete in nearly half the time. Such an advantage is a result of the increased efficiency afforded by the SPPs, without a concomitant loss of selectivity.

Figure 18:
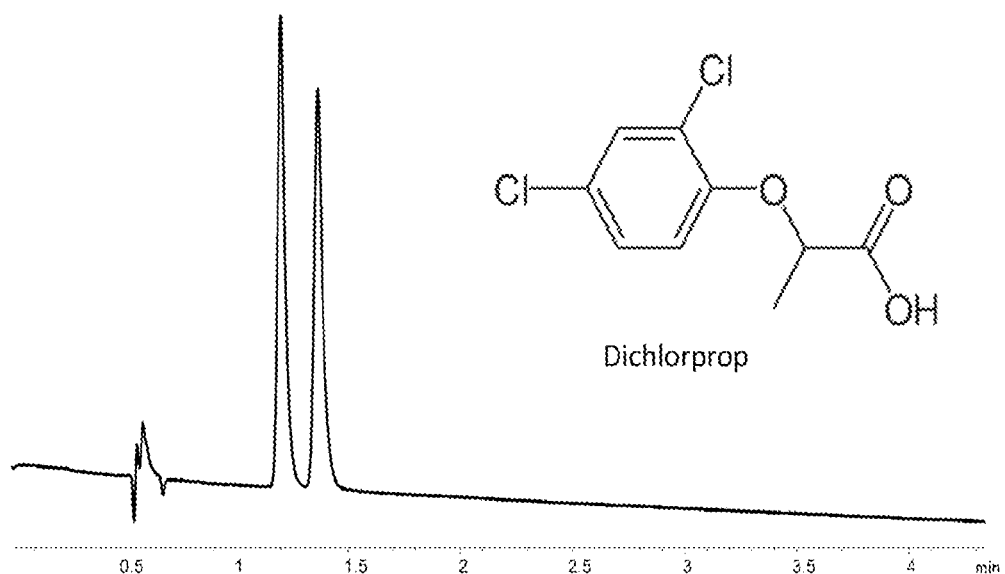
FIG. 18: example of a high efficiency, high speed, enantiomeric separation using t-butylcarbamoylated quinine based SPP CSP.

FIG. 18 shows an example of a high efficiency, high speed, enantiomeric separation using a t-butylcarbamoylated quinine based SPP CSP. 20:80 100 mM NH4OAc: MeOH (mixture $pH_a$ 6.0 adjusted with acetic acid), 1.0 mL/min, 22° C.

Figure 19:
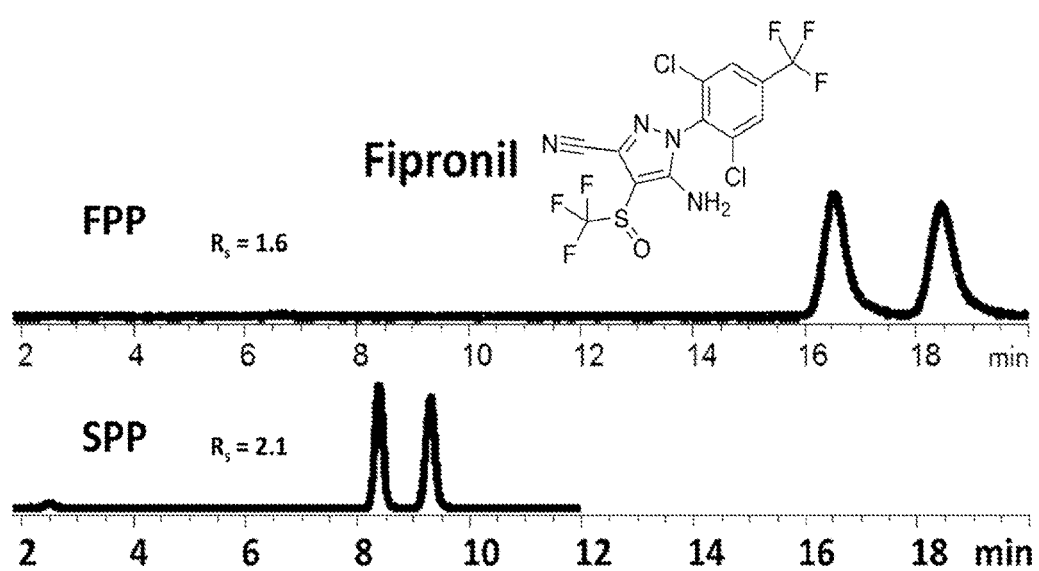
FIG. 19: separation of fipronil enantiomers.

FIG. 19 shows separation of fipronil enantiomers using an isopropylated cyclofructan 6 chiral selector bound to FPPs and SPPs. The mobile phase was heptane/ethanol (95/5). Note the increased resolution and efficiency when using the SPP-CSP. Also, the analysis time was considerably shorter for the separation performed using the SPP-CSP. The advantages are a result of the increased efficiency afforded by the SPPs, without a concomitant loss of selectivity.

Figure 20:
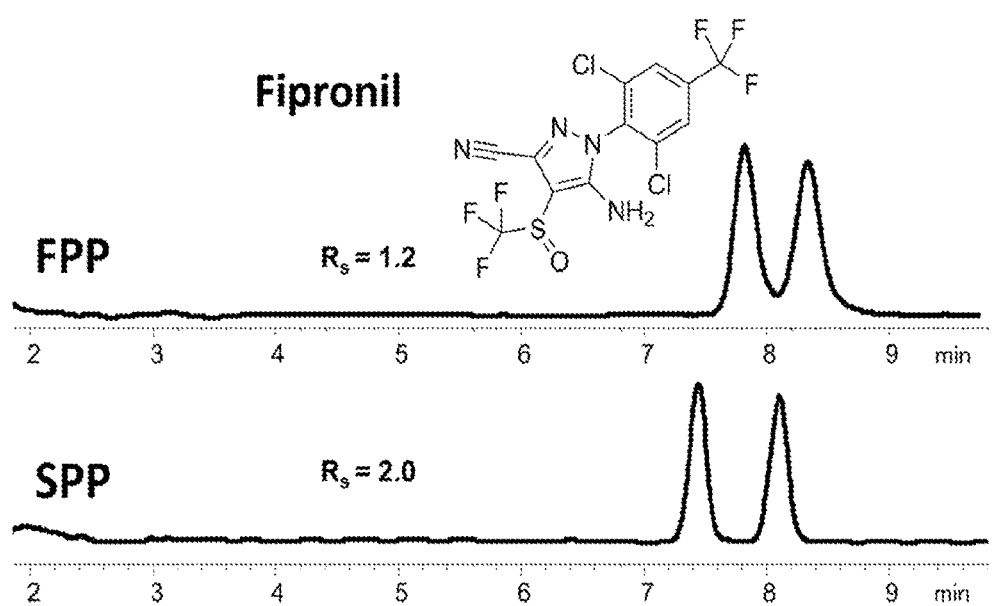
FIG. 20: constant retention comparison of the enantiomeric separation of fipronil.

FIG. 20 shows constant retention comparison of the enantiomeric separation of fipronil using an isopropylated chiral selector bound to FPPs and SPPs. The mobile phase composition was changed to allow all compounds to have similar retention. For the FPP chromatogram the mobile phase was heptane/ethanol (92/8). For the SPP chromatogram the mobile phase composition was heptane/ethanol (95/5). The flow rate in both cases was 1.0 mL/min. This example clearly demonstrates the overall gains in separation performance when using the SPP-CSPs. Note the large increase in resolution for the SPP-CSP.

Figure 21:
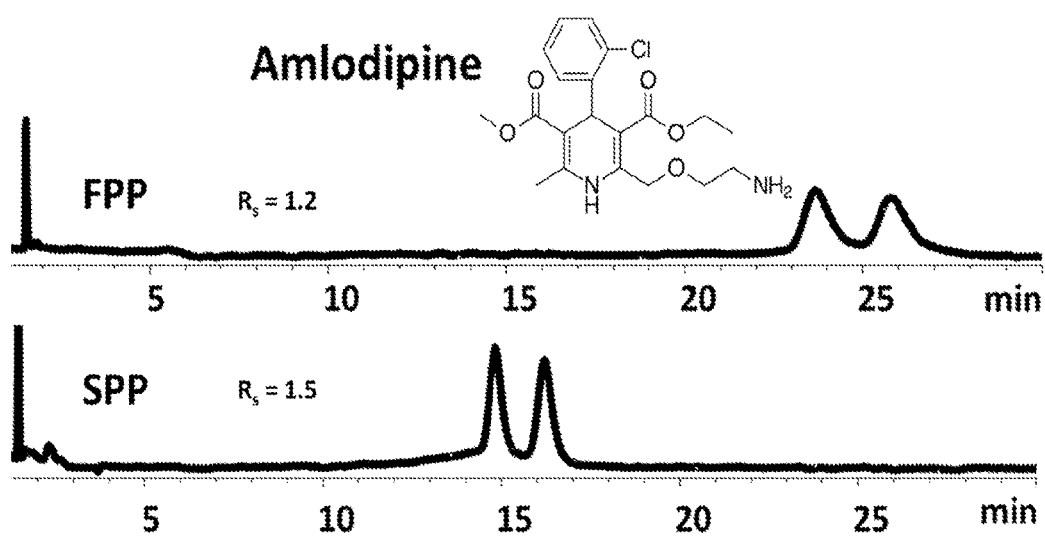
FIG. 21: separation of amlodipine enantiomers.

FIG. 21 shows separation of amlodipine enantiomers using an isopropylated cyclofructan 6 chiral selector bound to FPPs and SPPs. The mobile phase was acetonitrile/methanol (80/20) with 0.3% of acetic acid (AA) and 0.2% triethylamine (TEA). Note the equivalent resolution observed in both chromatograms, while the separation using the SPP-CSP was complete in nearly half the time. Such an advantage is a result of the increased efficiency afforded by the SPPs, without a concomitant loss of selectivity.

Figure 22:
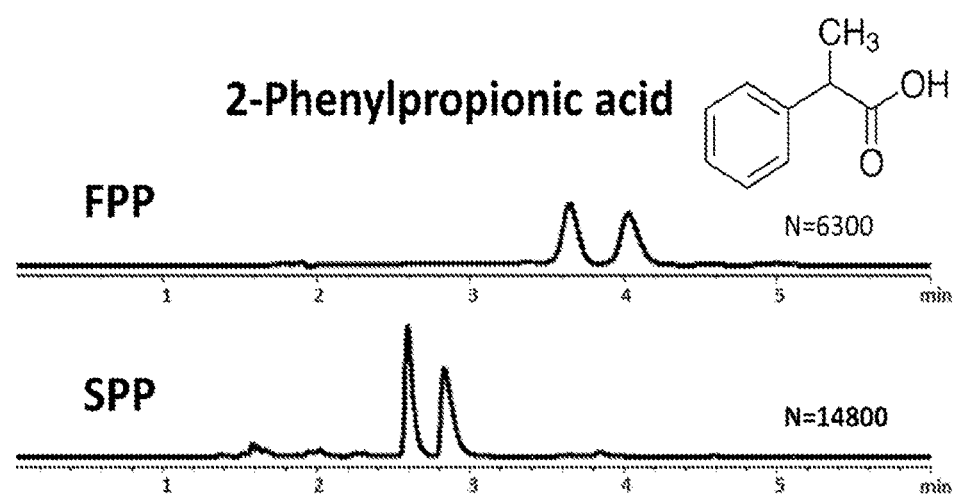
FIG. 22: separation of 2-phenylpropionic acid enantiomers.

FIG. 22 shows separation of 2-phenylpropionic acid enantiomers using a hydroxypropyl-β-cyclodextrin chiral selector bound to FPPs and SPPs. The mobile phase was 10 mM NH4OAc (pH 4.1)/ACN (75/25), flow rate: 1.0 mL/min. Note the equivalent resolution observed in both chromatograms, while the separation using the SPP-CSP was complete in nearly half the time. Such an advantage is a result of the increased efficiency afforded by the SPPs, without a concomitant loss of selectivity.

Figure 23:
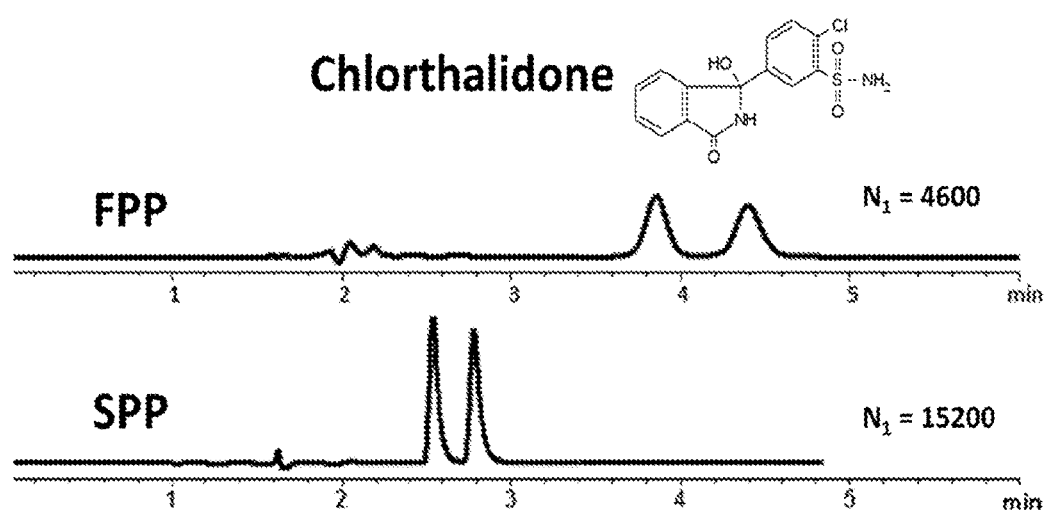
FIG. 23: separation of chlorthaldone enantiomers.

FIG. 23 shows separation of chlorthaldone enantiomers using a hydroxypropyl-β-cyclodextrin chiral selector bound to FPPs and SPPs. The mobile phase was 10 mM NH4OAc (pH 4.1)/ACN (85/15), flow rate: 1.0 mL/min. Note the baseline resolution observed in both chromatograms, while the separation using the SPP-CSP was complete in nearly half the time. Such an advantage is a result of the increased efficiency afforded by the SPPs, without a concomitant loss of selectivity.

Figure 24:
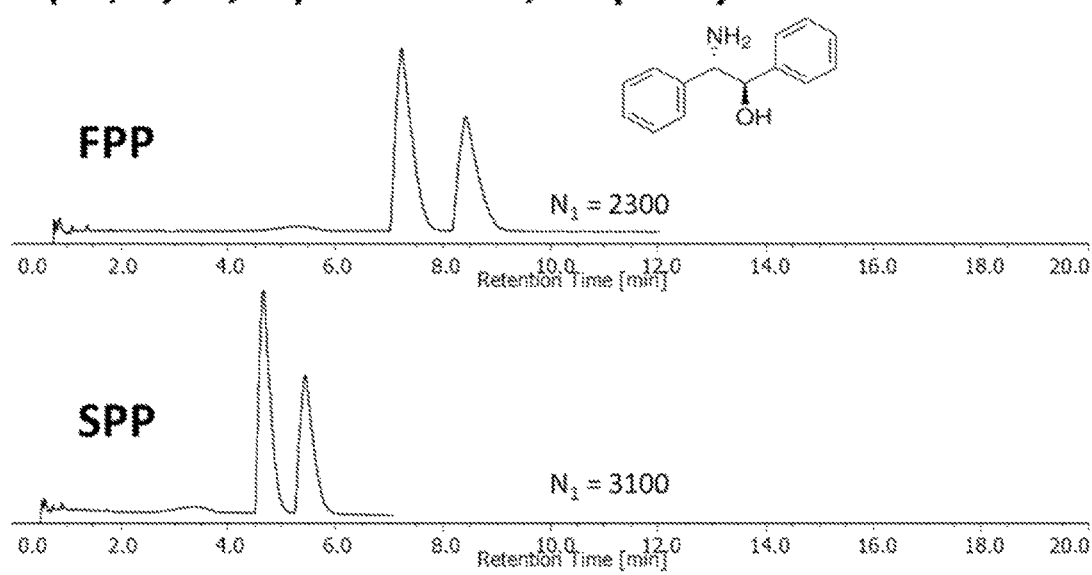
FIG. 24: supercritical fluid chromatography (SFC) separation of (1R,2S/1S,2R)-2-amino-1,2-diphenylethanol enantiomers.

FIG. 24 shows the SFC separation of (1R,2S/1S,2R)-2-amino-1,2-diphenylethanol enantiomers using an isopropylated cyclofructan 6 chiral selector bound to FPPs and SPPs in SFC. The mobile phase was carbon dioxide/methanol (80/20) with 0.3% of TFA and 0.2% TEA added to the methanol. Note the increased resolution and efficiency when using the SPP-CSP. Also, the analysis time was considerably shorter for the separation performed using the SPP-CSP. The advantages are a result of the increased efficiency afforded by the SPPs, without a concomitant loss of selectivity.

Figure 25:
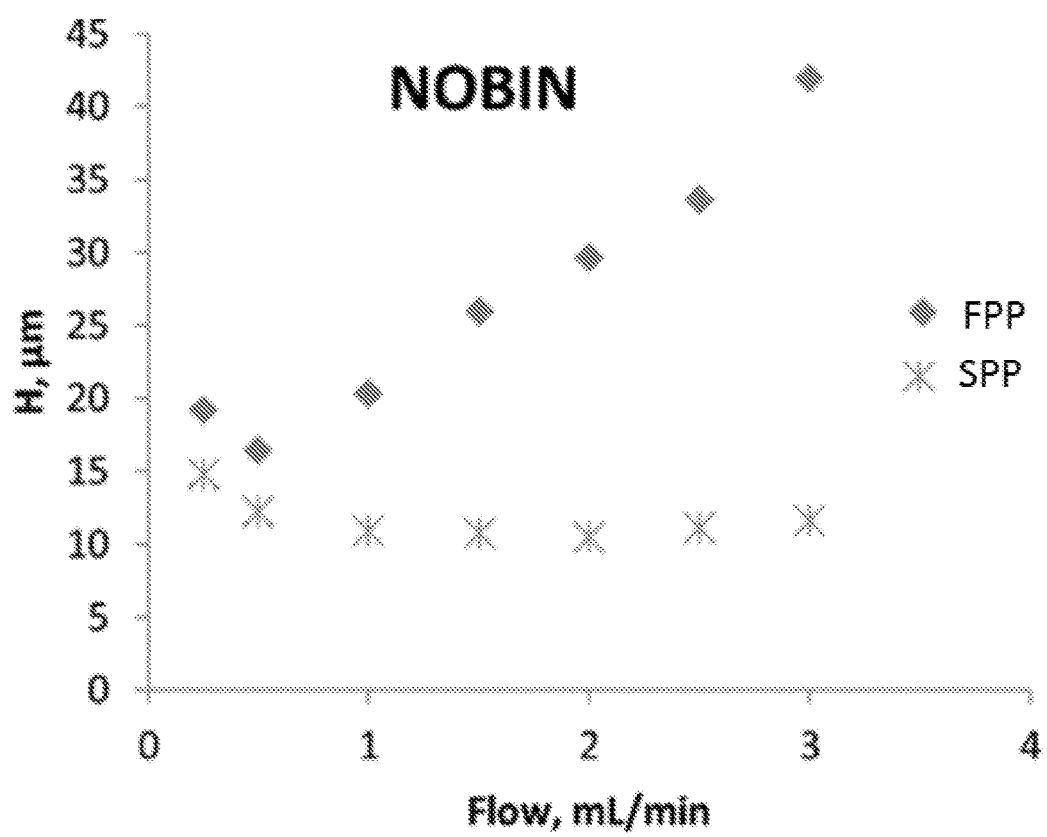
FIG. 25: dependence of plate height for NOBIN.

All of the advantages shown above for the SPP based stationary phases are because of their distinct structure relative to FPPs. FIG. 25 is a van Deemter plot of the height equivalent to a theoretical plate (H) vs. linear velocity of the mobile phase. A smaller 'H' is better and a less steep rise in the curve at higher flow is better. Clearly the SPPs performed much better in such a kinetic analysis. Dependence of plate height (based on first eluted enantiomer) for NOBIN on the flow rate for FPP-CSPs and SPP-CSPs. Separation conditions are the same for both CSPs. A bound isopropylated cyclofructan 6 chiral selector was used. It is important to note that the decrease in efficiency is attenuated at higher flow rates (e.g. 3.0 mL/min) for the SPP based CSP, which is a great advantage when doing fast separation.

Figure 26:
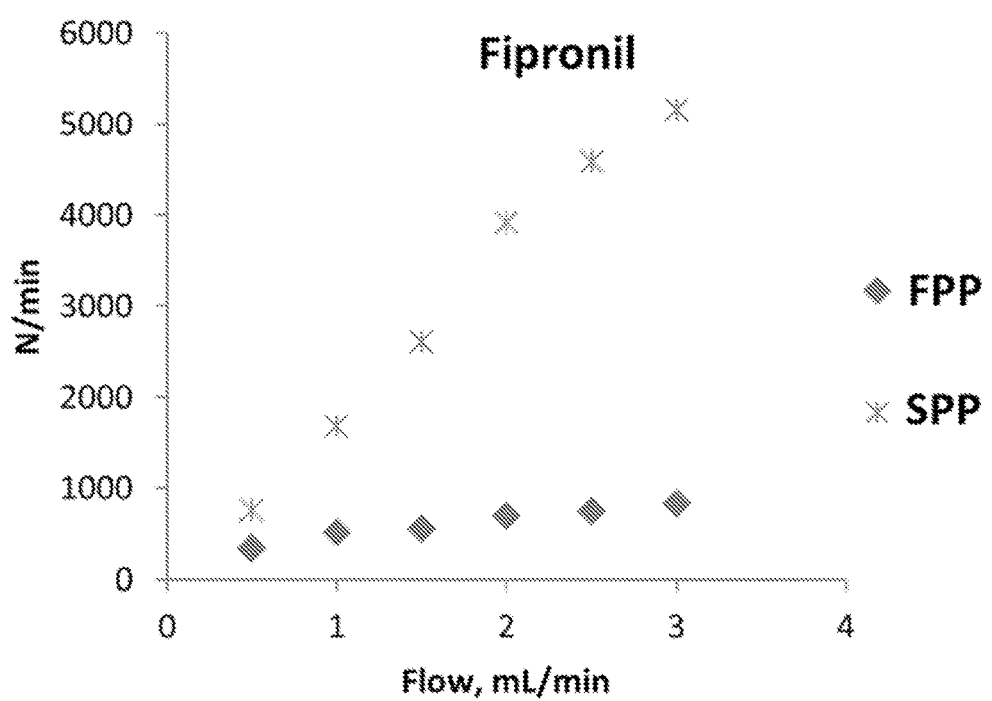
FIG. 26: dependence of efficiency per analysis time for fipronil on the flow rate for FPP-CSPs and SPP-CSPs.

FIG. 26 is a plot of dependence of efficiency per analysis time (based on first eluted enantiomer) for fipronil on the flow rate for FPP-CSPs and SPP-CSPs. It is clearly shown that the SPP is superior. Separation conditions were the same on each CSP. A bound isopropylated cyclofructan 6 chiral selector was used in both cases. It is important to note that the improvement in efficiency per analysis time is accentuated at higher flow rates (e.g. 3 mL/min) for the SPP based CSP. This advantage is useful for high throughput analyses of large numbers of compounds.

Figure 27:
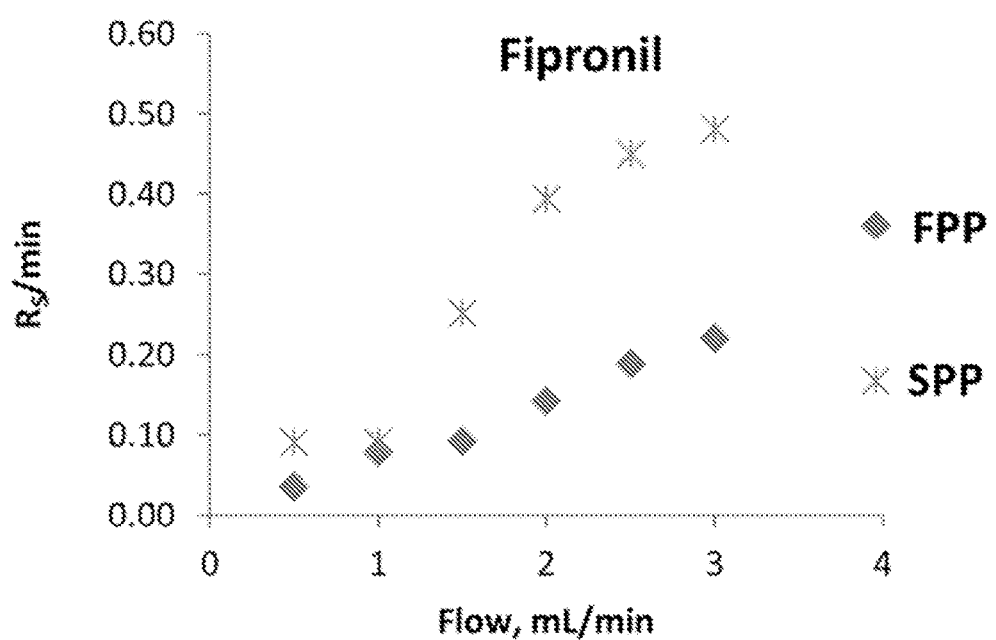
FIG. 27: dependence of resolution of fipronil on the flow rate for FPP-CSPs and SPP-CSPs.

FIG. 27 is a plot of enantiomeric resolution (Rs) per time vs. flow. Again, the SPP is far superior. Dependence of resolution (based on first eluted enantiomer) for fipronil on the flow rate for FPP-CSPs and SPP-CSPs shows the superiority of SPP-CSPs. Separation conditions were the same for each CSP. A bound isopropylated cyclofructan 6 chiral selector was used in both cases. It is important to note that the improvement in resolution per analysis time is accentuated at higher flow rates (e.g. 3 mL/min). This advantage is useful for high throughput analyses of large numbers of compounds.

Because of the extraordinarily high efficiency of CSPs made with SPPs and the fact that columns containing them have lower back pressures than columns containing <2 micron diameter FPPs, we are able to easily do ultrafast chiral separations on our SPPs. Examples are given in FIGS. 28-34 for SPP-CSPs made with different chiral selectors.

Figure 28:
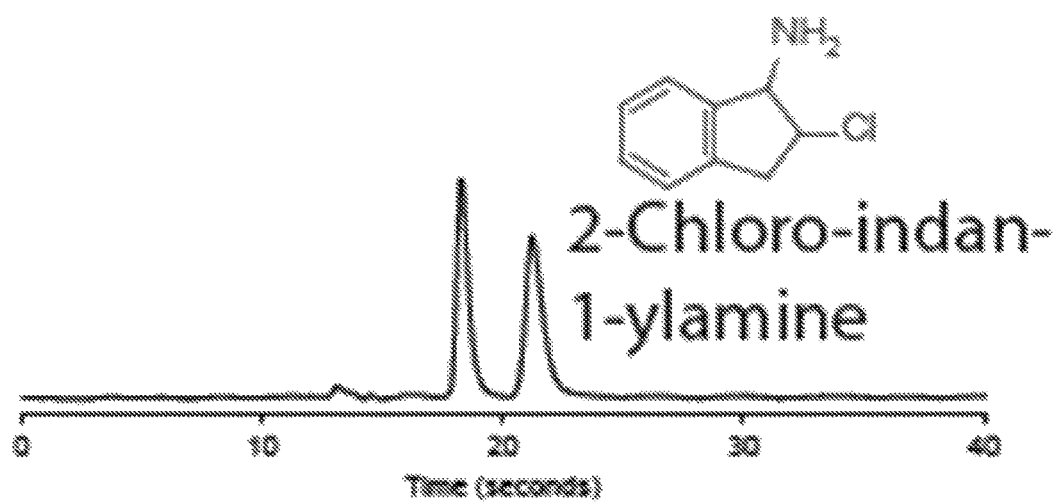
FIG. 28: example of a high efficiency, high speed, enantiomeric separation using an isopropylated cyclofructan 6 based SPP CSP.

FIG. 28 shows an example of a high efficiency, high speed, enantiomeric separation using an isopropylated cyclofructan 6 based SPP CSP. ACN/MeOH/TFA/TEA, 70/30/0.3/0.2, 4.5 mL/min, 22° C.

Figure 29:
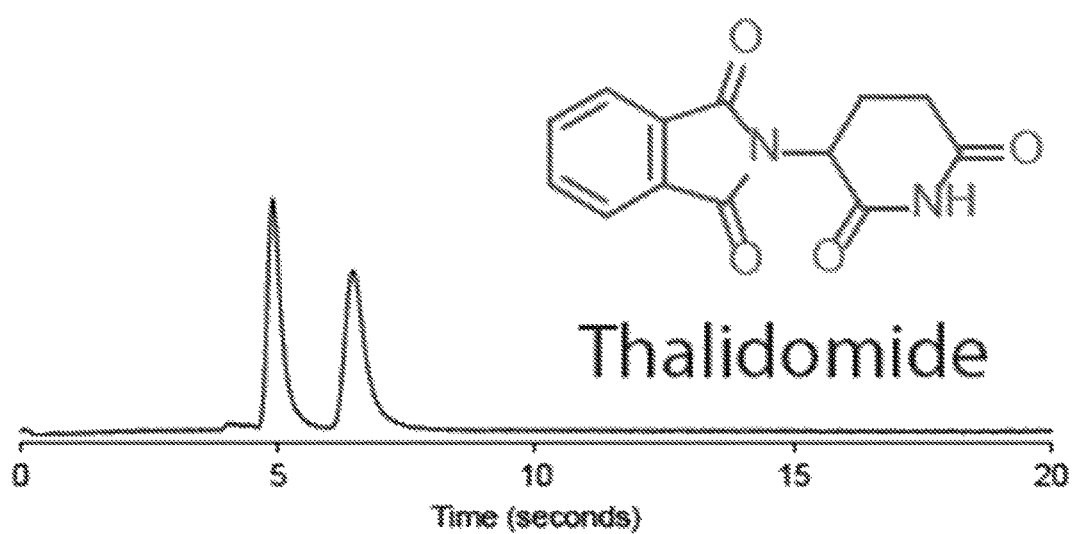
FIG. 29: example of a high efficiency, high speed, enantiomeric separation using a vancomycin based SPP CSP.

FIG. 29 shows an example of a high efficiency, high speed, enantiomeric separation using a vancomycin based SPP CSP. MeOH, 5.0 mL/min, 60° C.

Figure 30:
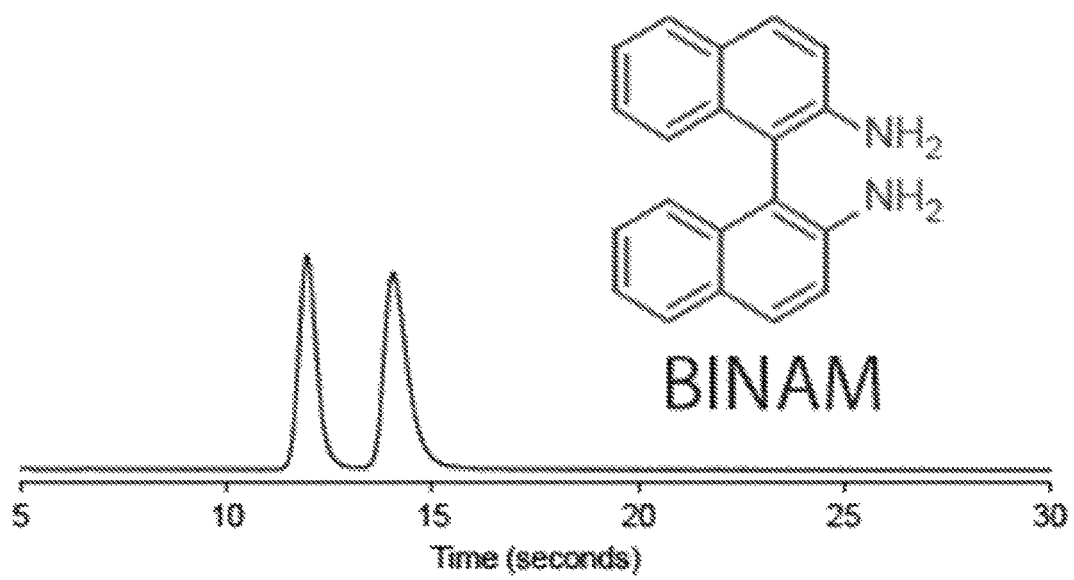
FIG. 30: example of a high efficiency, high speed, enantiomeric separation using a 3,5-dimethylphenyl carbamoyl cyclofructan 7 based SPP CSP.

FIG. 30 shows an example of a high efficiency, high speed, enantiomeric separation using a 3,5-dimethylphenyl carbamoylated cyclofructan 7 based SPP CSP. Hetp/EtOH, 90/10, 4.8 mL/min, 22° C.

Figure 31:
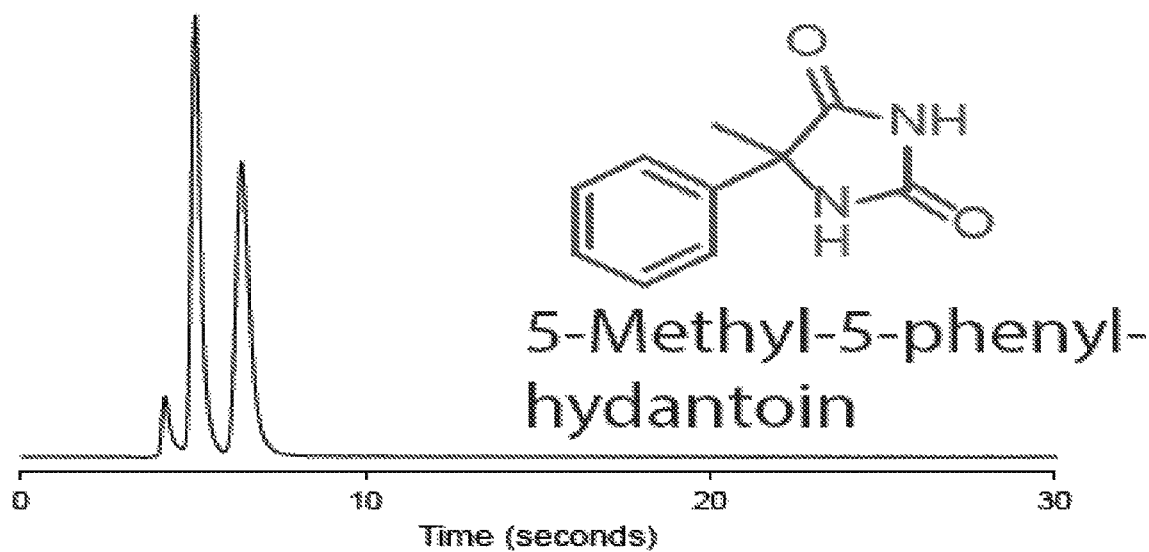
FIG. 31: example of a high efficiency, high speed, enantiomeric separation using a teicoplanin aglycone based SPP.

FIG. 31 shows an example of a high efficiency, high speed, enantiomeric separation using a teicoplanin aglycone based SPP. MeOH, 4.7 mL/min, 60° C.

Figure 32:
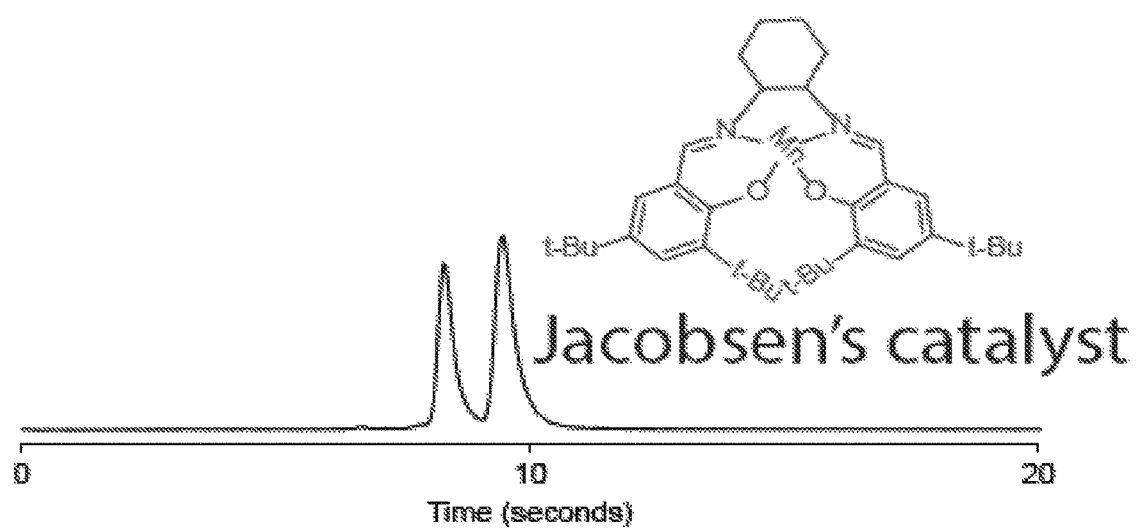
FIG. 32: example of a high efficiency, high speed, enantiomeric separation using a hydroxypropylate-β-cyclodextrin based SPP.

FIG. 32 shows an example of a high efficiency, high speed, enantiomeric separation using a hydroxypropylated-β-cyclodextrin based SPP. ACN/MeOH/TFA/TEA, 97/3/0.3/0.2, 4.8 mL/min, 60° C.

Figure 33:
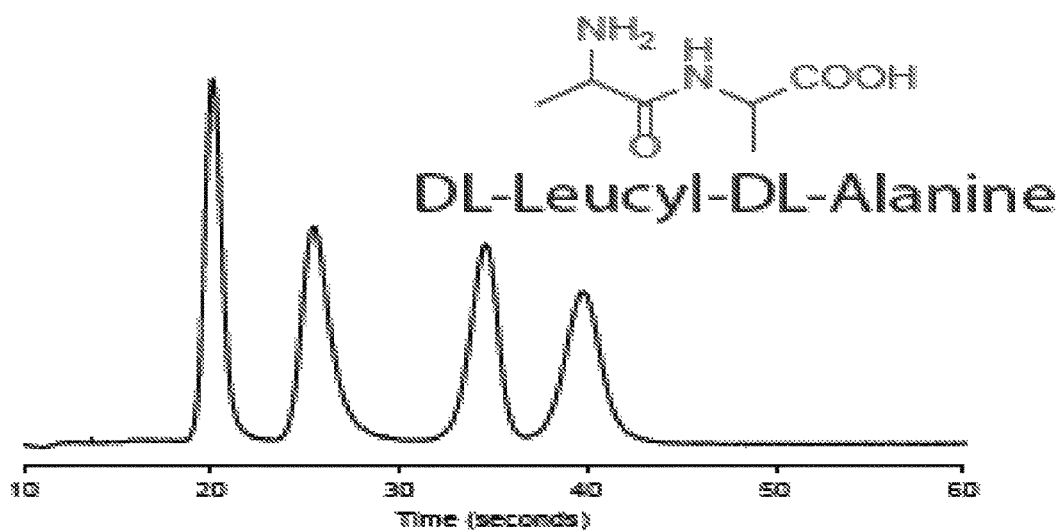
FIG. 33: example of a high efficiency, high speed, enantiomeric separation using a teicoplanin based SPP.

FIG. 33 shows an example of a high efficiency, high speed, enantiomeric separation using a teicoplanin based SPP. Water/MeOH, 60/40, 3.0 mL/min, 22° C.

Figure 34:
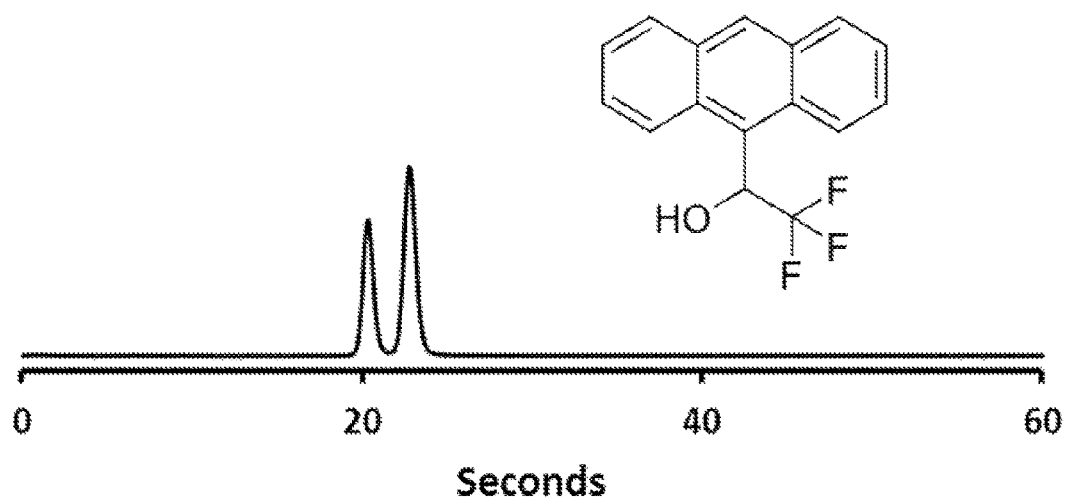
FIG. 34: example of a high efficiency, high speed, enantiomeric separation using a DNB-phenylglycine based SPP CSP.

FIG. 34 shows an example of a high efficiency, high speed, enantiomeric separation using a DNB-phenylglycine based SPP CSP. 95:5 heptane:ethanol, 5.0 mL/min, 22° C.

The following are some embodiments according to the present invention.

Embodiment 1

A stationary phase comprising a support and a chiral stationary phase.

Embodiment 2

The stationary phase according to embodiment 1, wherein the support comprises superficially porous particles (SPPs).

Embodiment 3

The stationary phase according to embodiment 1, wherein the chiral stationary phase comprises chiral selectors.

Embodiment 4

The stationary phase according to embodiment 2, wherein the SPP has a particle diameter from about 0.5 microns to about 20 microns.

Embodiment 5

The stationary phase according to embodiment 2, wherein the SPP has a particle diameter from about 1.3 microns to about 10 microns.

Embodiment 6

The stationary phase according to embodiment 2, wherein the SPP has a particle diameter from about 1.7 microns to about 5.0 microns.

Embodiment 7

The stationary phase according to embodiment 2, wherein the SPP has a particle diameter selected from among about 1.7, about 2.7 and about 4.0 microns.

Embodiment 8

The stationary phase according to embodiment 2, wherein the SPP has a particle diameter of about 1.7 microns.

Embodiment 9

The stationary phase according to embodiment 2, wherein the SPP has a particle diameter of about 2.7 microns.

Embodiment 10

The stationary phase according to embodiment 2, wherein the SPP has a particle diameter of about 4.0 microns.

Embodiment 11

The stationary phase according to embodiment 2, wherein the SPP has a pore size from about 100 angstroms to about 300 angstroms.

Embodiment 12

The stationary phase according to embodiment 2, wherein the SPP has a pore size from about 100 angstroms to about 150 angstroms.

Embodiment 13

The stationary phase according to embodiment 2, wherein the SPP has a pore size from about 110 angstroms to about 130 angstroms.

Embodiment 14

The stationary phase according to embodiment 2, wherein the SPP has a pore size of about 120 angstroms.

Embodiment 15

The stationary phase according to embodiment 2, wherein the SPP has a surface area from about 150 m$^2$/g to about 500 m$^2$/g.

Embodiment 16

The stationary phase according to embodiment 2, wherein the SPP has a surface area of about 120 m$^2$/g.

Embodiment 17

The stationary phase according to embodiment 3, wherein the chiral selectors are covalently bonded to the SPP.

Embodiment 18

The stationary phase according to embodiment 3, wherein the chiral selectors are selected from among of oligosaccharides and derivatives, cyclic oligosaccharides and derivatives, peptides and derivatives, glycopeptides and derivatives, macrocyclic glycopeptides and derivatives, pi-complexes, chiral crown ethers, ligand exchangers and ion exchangers.

Embodiment 19

The stationary phase according to embodiment 3, wherein the chiral selectors are selected from among of cyclodextrins, derivatized cyclodextrins, cyclofructans, derivatized cyclofructans, teicoplanin, vancomycin, teicoplanin aglycone, ristocetin A, dalbavancin, boromycin, DNB-phenylglycine, DNB-diphenylethylenediamine, DNB-N-(1,2,3,4-tetrahydrophenanthren-4-yl)benzamide, DNB-1,2-diaminocyclohexane, 3,3'-diphenyl-binaphthyl functionalized 18-crown-6, proline, penicillamine, hydroxyproline, quinine, derivatized quinine, quinidine and derivatized quinidine.

Embodiment 20

A superficially porous particle based chiral stationary phase comprising a chiral selector linked to the superficially porous particle.

Embodiment 21

The superficially porous particle of embodiment 20, wherein the chiral selectors are covalently bonded to the SPP.

Embodiment 22

The superficially porous particle of embodiment 20, wherein the chiral selectors are selected from among of oligosaccharides and derivatives, cyclic oligosaccharides and derivatives, peptides and derivatives, glycopeptides and derivatives, macrocyclic glycopeptides and derivatives, pi-complexes, chiral crown ethers, ligand exchangers and ion exchangers.

Embodiment 23

The superficially porous particle of embodiment 20, wherein the chiral selectors are selected from among of cyclodextrins, derivatized cyclodextrins, cyclofructans, derivatized cyclofructans, teicoplanin, vancomycin, teicoplanin aglycone, ristocetin A, dalbavancin, boromycin, DNB-phenylglycine, DNB-diphenylethylenediamine, DNB-N-(1,2,3,4-tetrahydrophenanthren-4-yl)benzamide, DNB-1,2-diaminocyclohexane, 3,3'-diphenyl-binaphthyl functionalized 18-crown-6, proline, penicillamine, hydroxyproline, quinine, derivatized quinine, quinidine and derivatized quinidine.

Embodiment 24

The superficially porous particle of embodiment 20, wherein the chiral selector is a native or derivatized cyclofructan or a native or derivatized cyclodextrin.

Embodiment 25

The superficially porous particle according to embodiment 24, wherein derivatizing groups of the derivatized cyclofructan and derivatized cyclodextrin are alkane (e.g. linear alkane C1-C30, branched alkane C1-C30, unsaturated alkane C1-C30, cyclic alkane C1-C30, linear and/or cyclic alkane containing heteroatoms (e.g. N, S, O) C1-C30) or aromatic (benzyl, derivatized benzyl (e.g. NO2, Cl, F, Br, CH3 functionalized), phenyl, derivatized phenyl (e.g. NO2, Cl, F, Br, CH3 functionalized), naphthyl, derivatized naphthyl (e.g. NO2, Cl, F, Br, CH3 functionalized), or biaryl).

Embodiment 26

The superficially porous particle according to embodiment 20, wherein the chiral selector linked to the superficially porous particle is bonded via ether, carbamate, thioether, thiocarbamate, ester, triazole, or urea linkages.

Embodiment 27

The superficially porous particle according to embodiment 20, wherein the chiral selector is selected from among macrocyclic glycopeptides, pi-complex, and anionic, cationic or zwitterionic exchange.

Embodiment 28

The superficially porous particle according to embodiment 27, wherein the macrocyclic glycopeptides are selected from among teicoplanin, boromycin, ristocetin A, dalbavancin, and vancomycin.

Embodiment 29

The superficially porous particle according to embodiment 27, wherein the pi-complex is dinitrobenzoyl phenylglycine.

Embodiment 30

The superficially porous particle according to embodiment 27, wherein the anionic exchange is t-butyl carbamoylated quinine.

Embodiment 31

A stationary phase support for liquid chromatographic chiral separation comprising superficially porous particle and chiral selectors.

Embodiment 32

A superficially porous particle having a medium or small size chiral selector bonded thereto producing superior chiral chromatographic results including higher efficiency, higher resolution, shorter retention time and equivalent to higher selectivity than conventional stationary phase support.

Embodiment 33

A stationary phase support for liquid chromatographic chiral separations comprising a support material and a specifically bonded or irreversibly adsorbed small to medium size chiral selectors to form brush type chiral superficially porous particles thereto, thereby producing superior chiral chromatographic results including higher efficiency, higher resolution and shorter retention time than conventional support.

Embodiment 34

A method for enantioseparation of at least one chiral molecule comprising contacting a mixture comprising chiral molecules with a superficially porous particle based chiral stationary phase such that enantiomers of the chiral molecules are separated.

Embodiment 35

A method of making a superficially porous particle chiral stationary phases comprising selecting a chiral selector from among of oligosaccharides and derivatives, cyclic oligosaccharides and derivatives, peptides and derivatives, glycopeptides and derivatives, macrocyclic glycopeptides and derivatives, pi-complexes, chiral crown ethers, ligand exchangers and ion exchangers; and covalently bonding the chiral selector to a superficially porous particle, thereby obtaining the superficially porous particle chiral stationary phases.

Although the preferred embodiments of the present invention have been described herein, the descriptions provided herein are merely illustrative. Further modification of the invention herein disclosed will occur to those skilled in the respective arts and all such modifications are deemed to be within the scope of the invention as defined by the attached claims.

What is claimed:

1. A stationary phase comprising
   a support comprising superficially porous particles (SPP); and
   a chiral stationary phase comprising non-polymeric chiral selectors,
   wherein
   the non-polymeric chiral selectors are covalently bonded to the SPP via ether, carbamate, thioether, thiocarbamate, ester, triazole, or urea linkage, and
   the SPP has a surface area from about 100 m$^2$/g to about 500 m$^2$/g.

2. The stationary phase according to claim 1, wherein the SPP has a particle diameter from about 0.5 microns to about 20 microns.

3. The stationary phase according to claim 1, wherein the SPP has a particle diameter selected from the group consisting of about 1.7, about 2.7 and about 4.0 microns.

4. The stationary phase according to claim 1, wherein the SPP has a pore size from about 100 angstroms to about 300 angstroms.

5. The stationary phase according to claim 1, wherein the SPP has a surface area of about 120 m$^2$/g.

6. The stationary phase according to claim 1, wherein the chiral selectors are selected from the group consisting of oligosaccharides and derivatives, cyclic oligosaccharides and derivatives, peptides and derivatives, glycopeptides and derivatives, macrocyclic glycopeptides and derivatives, pi-complexes, chiral crown ethers, ligand exhangers and ion exchangers.

7. The stationary phase according to claim 1, wherein the chiral selectors are selected from the group consisting of cyclodextrins, derivatized cyclodextrins, cyclofructans, derivatized cyclofructans, teicoplanin, vancomycin, teicoplanin aglycone, ristocetin A, dalbavancin, boromycin, DNB-phenylglycine, DNB-diphenylethylenediamine, DNB-N-(1,2,3,4-tetrahydrophenanthren-4-yl)benzamide, DNB-1,2-diaminocyclohexane, 3,3'-diphenyl-binaphthyl funcionalized 18-crown-6, proline, penicillamine, hydroxyproline, quinine, derivatized quinine, quinidine and derivatized quinidine.

8. A superficially porous particle based chiral stationary phase comprising a non-polymeric chiral selector covalently linked to the superficially porous particle via ether, carbamate, thioether, thiocarbamate, ester, triazole, or urea linkage.

9. The superficially porous particle of claim 8, wherein the chiral selectors are selected from the group consisting of oligosaccharides and derivatives, cyclic oligosaccharides and derivatives, peptides and derivatives, glycopeptides and derivatives, macrocyclic glycopeptides and derivatives, pi-complexes, chiral crown ethers, ligand exhangers and ion exchangers.

10. The superficially porous particle of claim 8, wherein the chiral selectors are selected from the group consisting of cyclodextrins, derivatized cyclodextrins, cyclofructans, derivatized cyclofructans, teicoplanin, vancomycin, teicoplanin aglycone, ristocetin A, dalbavancin, boromycin, DNB-phenylglycine, DNB-diphenylethylenediamine, DNB-N-(1,2,3,4-tetrahydrophenanthren-4-yl)benzamide, DNB-1,2-diaminocyclohexane, 3,3'-diphenyl-binaphthyl funcionalized 18-crown-6, proline, penicillamine, hydroxyproline,quinine, derivatized quinine, quinidine and derivatized quinidine.

11. The superficially porous particle of claim 8, wherein the chiral selector is native or derivatized cyclodextrins, or native or derivatized cyclofructans.

12. The superficially porous particle according to claim 11, wherein derivatizing groups of the derivatized cyclodextrin and the derivatized cyclofructan are alkanes or aromatic compounds.

13. The superficially porous particle according to claim 8, wherein the chiral selector is selected from the group consisting of macrocyclic glycopeptides, pi-complex, and anionic, cationic or zwitterionic exchange.

14. The superficially porous particle according to claim 13, wherein the macrocyclic glycopeptides are selected from the group consisting of teicoplanin, boromycin, ristocetin A, dalbavancin, and vancomycin.

15. The superficially porous particle according to claim 13, wherein the pi-complex is dinitrobenzoyl phenylglycine.

16. The superficially porous particle according to claim 13, wherein the anionic exchange is t-butyl carbamoylated quinine.

17. A method of making the superficially porous particle based chiral stationary phase according to claim 8 comprising
   selecting the non-polymeric chiral selector from the group consisting of oligosaccharides and derivatives, cyclic oligosaccharides and derivatives, peptides and derivatives, glycopeptides and derivatives, macrocyclic glycopeptides and derivatives, pi-complexes, chiral crown ethers, ligand exchangers and ion exchangers; and covalently bonding the chiral selector to the superficially porous particle, thereby obtaining the superficially porous particle chiral stationary phase.

18. The superficially porous particle according to claim 12, wherein the alkanes are selected from the group consisting of linear alkane C1-C30; branched alkane C1-C30; unsaturated alkane C1-C30; cyclic alkane C1-C30; linear and/or cyclic alkane C1-C30 containing heteroatoms, wherein the heteroatoms are selected from the group consisting of N, S, O, and wherein the aromatic compounds are selected from the group consisting of benzyl; derivatized benzyl, wherein the derivatized benzyl is $NO_2$, Cl, F, Br, or $CH_3$ functionalized benzyl; phenyl; derivatized phenyl, wherein the derivatized phenyl is $NO_2$, Cl, F, Br, or $CH_3$ functionalized phenyl; naphthyl; derivatized naphthyl, wherein the derivatized naphthyl is NO2, Cl, F, Br, or CH3 functionalized naphthyl, or biaryl.

* * * * *